(12) United States Patent
Yabunouchi et al.

(10) Patent No.: US 8,044,222 B2
(45) Date of Patent: Oct. 25, 2011

(54) AROMATIC AMINE DERIVATIVES AND ORGANIC ELECTROLUMINESCENT DEVICE USING SAME

(75) Inventors: Nobuhiro Yabunouchi, Chiba (JP); Masahiro Kawamura, Chiba (JP); Hisayuki Kawamura, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 1010 days.

(21) Appl. No.: 11/834,157

(22) Filed: Aug. 6, 2007

(65) Prior Publication Data

US 2008/0108839 A1 May 8, 2008

(30) Foreign Application Priority Data

Aug. 23, 2006 (JP) .................................. 2006-226121

(51) Int. Cl.
*C07D 307/38* (2006.01)
(52) U.S. Cl. ......................................................... 549/491
(58) Field of Classification Search .................... 549/491
See application file for complete search history.

(56) References Cited

FOREIGN PATENT DOCUMENTS

| | | |
|---|---|---|
| EP | 1 559 706 A1 | 8/2005 |
| JP | 04-224572 | 8/1992 |
| JP | 7-287408 | 10/1995 |
| JP | 10-125468 | 5/1998 |
| JP | 10-265773 | 10/1998 |
| JP | 2000-319273 | 11/2000 |
| WO | WO 01/53286 A1 | 7/2001 |
| WO | WO 2004/058740 A1 | 7/2004 |
| WO | 2006/046441 A1 | 5/2006 |
| WO | WO 2006/073054 A1 | 7/2006 |

OTHER PUBLICATIONS

King, Med. Chem. Principle and Practice (1994), pp. 206-208.*
U.S. Appl. No. 11/834,203, filed Aug. 6, 2007, Yabunouchi, et al.
U.S. Appl. No. 11/854,162, filed Sep. 12, 2007, Morishita, et al.
Hitoshi Ohishi, et al. "Amorphous Molecular Materials with High Carrier Mobilities: Thiophene- and Selenophene-Containing Tris(oligoarylenyl)amines" The Chemical Society of Japan, Chemistry Letters vol. 33, No. 10, 2004, pp. 1266-1267.

* cited by examiner

*Primary Examiner* — Taofiq A Solola
(74) *Attorney, Agent, or Firm* — Oblon, Spivak, McClelland, Maier & Neustadt, L.L.P.

(57) ABSTRACT

The present invention provides a novel aromatic amine derivative having a specific structure and an organic electroluminescence device in which an organic thin film layer comprising a single layer or plural layers including at least a light emitting layer is interposed between a cathode and an anode, wherein at least one layer in the above organic thin film layer, particularly a hole transporting layer contains the aromatic amine derivative described above in the form of a single component or a mixed component. Use of the aromatic amine derivative described above materialize an organic electroluminescence device which reduces an operating voltage and makes molecules less liable to be crystallized and which enhances a yield in producing the organic EL device and has a long lifetime.

20 Claims, No Drawings

AROMATIC AMINE DERIVATIVES AND ORGANIC ELECTROLUMINESCENT DEVICE USING SAME

BACKGROUND OF THE INVENTION

The present invention relates to an aromatic amine derivative and an organic electroluminescence (EL) device using the same, specifically to an aromatic amine derivative which reduces the operating voltage and inhibits the molecules from being crystallized by using an aromatic amine derivative having a specific substituent for a hole transporting material and which enhances a yield in producing an organic EL device and improves a lifetime of the organic EL device.

RELATED ART

An organic EL device is a spontaneous light emitting device making use of the principle that a fluorescent substance emits light by recombination energy of holes injected from an anode and electrons injected from a cathode by applying an electric field. Since an organic EL device of a laminate type driven at a low voltage was reported by C. W. Tang et al. of Eastman Kodak Company (C. W. Tang and S. A. Vanslyke, Applied Physics Letters, Vol. 51, p. 913, 1987 and the like), researches on organic EL devices comprising organic materials as structural materials have actively been carried out. Tang et al. use tris(8-quinolinolate) aluminum for the light emitting layer and a triphenyldiamine derivative for the hole transporting layer. The advantages of the laminate structure include an elevation in an efficiency of injecting holes into a light emitting layer, a rise in a production efficiency of excitons produced by blocking electrons injected from a cathode to recombine them and shutting up of excitons produced in a light emitting layer. As shown in the above example, a two-layer type comprising a hole transporting (injecting) layer and an electron transporting and light emitting layer and a three-layer type comprising a hole transporting (injecting) layer, a light emitting layer and an electron transporting (injecting) layer are well known as the device structures of an organic EL device. In such laminate type structural devices, device structures and forming methods are studied in order to enhance a recombination efficiency of holes and electrons injected.

Usually, when an organic EL device is operated or stored under high temperature environment, brought about are adverse effects such as a change in a color of emitted light, a reduction in a current efficiency, a rise in an operating voltage and a reduction in an emission lifetime. A glass transition temperature (Tg) of a hole transporting material has to be raised in order to prevent the above matters. Accordingly, the hole transporting material has to have a lot of aromatic groups in a molecule (for example, aromatic diamine derivatives described in Patent Document 1 and aromatic fused ring diamine derivatives described in Patent Document 2), and usually structures having 8 to 12 benzene rings are preferably used.

However, if they have a lot of aromatic groups in a molecule, crystallization is liable to be caused in forming a thin film using the above hole transporting materials to produce an organic EL device, and the problems that an outlet of a crucible used for vapor deposition is clogged and that defects of a thin film originating in crystallization are caused to bring about a reduction in a yield of an organic EL device have been brought about. Further, compounds having more aromatic groups in a molecule have usually a higher glass transition temperature (Tg) but have a higher sublimation temperature, and it is considered that the phenomena that decomposition is caused in vapor deposition and that a deposited film is unevenly formed are brought about, so that the problem that the lifetime is short has been involved therein.

On the other hand, a publicly known document in which asymmetric aromatic amine derivatives are disclosed is available. For example, aromatic amine derivatives having an asymmetric structure are described in Patent Document 3, but no specific examples are found therein, and the characteristics of the asymmetric compounds are not described therein at all. Further, the examples of asymmetric aromatic amine derivatives having phenanthrene are described in Patent Document 4, but they are handled on the same basis as symmetric compounds, and the characteristics of the asymmetric compounds are not described therein at all. Also, a specific synthetic process is necessary for the asymmetric compounds, but descriptions on the production processes of the asymmetric compounds are not clearly shown in the above patents. Further, a production process of aromatic amine derivatives having an asymmetric structure is described in Patent Document 5, but the characteristics of the asymmetric compounds are not described therein. Thermally stable asymmetric compounds having a high glass transition temperature are described in Patent Document 6, but only examples of compounds having carbazole are shown.

Further, compounds having furan are reported in Patent Document 7, but only compounds in which furan is bonded directly to amine are described. Also, compounds in which furan is bonded to nitrogen via an aryl group are described in Patent Documents 7 to 9, but the satisfactory performances are not obtained. Accordingly, an organic EL device having more excellent performances has been strongly required to be developed.

Patent Document 1: U.S. Pat. No. 4,720,432
Patent Document 2: U.S. Pat. No. 5,061,569
Patent Document 3: Japanese Patent Application Laid-Open No. 48656/1996
Patent Document 4: Japanese Patent Application Laid-Open No. 135261/1999
Patent Document 5: Japanese Patent Application Laid-Open No. 171366/2003
Patent Document 6: U.S. Pat. No. 6,242,115
Patent Document 7: Japanese Patent Application Laid-Open No. 319273/2000
Patent Document 8: Japanese Patent Application Laid-Open No. 125468/1998
Patent Document 9: Japanese Patent Application Laid-Open No. 224572/1992

DISCLOSURE OF THE INVENTION

The present invention has been made in order to solve the problems described above, and an object thereof is to provide an organic EL device which reduces an operating voltage and makes molecules less liable to be crystallized and which is improved in a yield in producing the organic EL device and has a long lifetime and an aromatic amine derivative which materializes the same.

Intensive researches repeated by the present inventors in order to achieve the object described above have resulted in finding that the above object can be achieved by using a novel aromatic amine derivative having a specific substituent represented by the following Formula (1) as a material for an organic EL device and using it particularly for a hole transporting material, and thus the present inventors have come to complete the present invention.

Further, it has been found that an amino group substituted with an aryl group having a furan structure represented by Formula (2) is suited as an amine unit having the specific substituent. The above amine unit has a polar group, so that it can be interacted with an electrode, and therefore it has the effects that charges are readily injected and that the operating voltage is reduced due to a high mobility since it has a furan structure. In addition thereto, the above amine unit has a steric hindrance, so that interaction between the molecules is small, and therefore it has the effects that crystallization thereof is inhibited to enhance a yield in producing an organic EL device and that the organic EL device obtained is extended in a lifetime. In particular, it has been found that a marked reduction in the voltage and an effect of extending the lifetime are obtained by combining with a blue light emitting device. Further, in the compounds having a large molecular weight, the compounds having an asymmetric structure can be reduced in a vapor deposition temperature, and therefore they can be inhibited from being decomposed in vapor deposition and can be extended in a lifetime.

That is, the present invention provides an aromatic amine derivative represented by the following Formula (1):

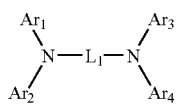

(1)

[wherein $L_1$ represents a substituted or non-substituted arylene group having 6 to 50 ring atoms;
at least one of $Ar_1$ to $Ar_4$ is represented by the following

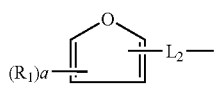

(2)

(wherein $R_1$ is a hydrogen atom, a substituted or non-substituted aryl group having 6 to 50 ring atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 2 to 50 carbon atoms, a halogen atom, a cyano group, a nitro group, a hydroxy group or a carboxyl group;
a is an integer of 0 to 3; and
$L_2$ represents a substituted or non-substituted arylene group having 6 to 50 ring atoms);
in Formula (1), among $Ar_1$ to $Ar_4$, the groups which are not represented by Formula (2) each are independently a substituted or non-substituted aryl group having 6 to 50 ring atoms;
provided that substituents for $Ar_1$ to $Ar_4$ are a substituted or non-substituted aryl group having 6 to 50 ring carbon atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 2 to 50 carbon atoms, a halogen atom, a cyano group, a nitro group, a hydroxy group or a carboxyl group].

Further, the present invention provides an aromatic amine derivative represented by any of the following Formulas (4) to (6):

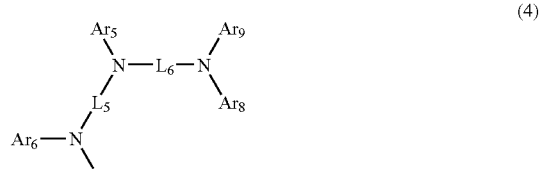

(4)

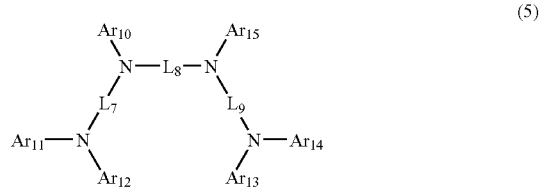

(5)

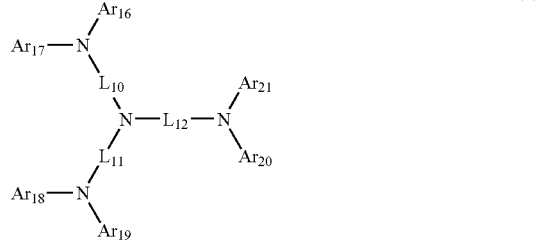

(6)

[wherein $L_5$ to $L_{12}$ represent a substituted or non-substituted arylene group having 6 to 50 ring atoms;
at least one of $Ar_5$ to $Ar_9$ is represented by the following Formula (7);
at least one of $Ar_{10}$ to $Ar_{15}$ is represented by the following Formula (7);
at least one of $Ar_{16}$ to $Ar_{21}$ is represented by the following Formula (7);

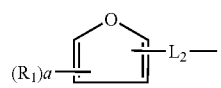

(7)

(wherein $R_1$ is a hydrogen atom, a substituted or non-substituted aryl group having 6 to 50 ring atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 2 to 50 carbon atoms, a halogen atom, a cyano group, a nitro group, a hydroxy group or a carboxyl group;
a is an integer of 0 to 3; and
$L_2$ represents a substituted or non-substituted arylene group having 6 to 50 ring atoms);
in the formulas, $Ar_5$ to $Ar_{21}$ each are independently a substituted or non-substituted aryl group having 6 to 50 ring atoms;
provided that substituents for $Ar_5$ to $Ar_{21}$ are a substituted or non-substituted aryl group having 6 to 50 ring atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 2 to 50 carbon atoms, a halogen atom, a cyano group, a nitro group, a hydroxy group or a carboxyl group].

Further, the present invention provides an organic EL device in which an organic thin layer comprising a single layer or plural layers including at least a light emitting layer is interposed between a cathode and an anode, wherein at least one layer in the above organic thin layer contains the aromatic amine derivative described above in the form of a single component or a mixed component.

The aromatic amine derivative of the present invention and the organic EL device obtained by using the same are reduced in an operating voltage, less liable to be crystallized in molecules, improved in a yield in producing the organic EL device and extended in lifetimes.

BEST MODE FOR CARRYING OUT THE INVENTION

The aromatic amine derivative of the present invention is represented by the following Formula (1):

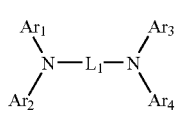
(1)

in Formula (1), $L_1$ represents a substituted or non-substituted arylene group having 6 to 50 ring atoms; at least one of $Ar_1$ to $Ar_4$ is represented by the following Formula (2):

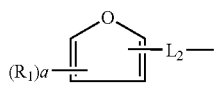
(2)

in Formula (2), $R_1$ is a hydrogen atom, a substituted or non-substituted aryl group having 6 to 50 ring atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 2 to 50 carbon atoms, a halogen atom, a cyano group, a nitro group, a hydroxy group or a carboxyl group; a is an integer of 0 to 3; $L_2$ represents a substituted or non-substituted arylene group having 6 to 50 ring atoms; in Formula (1), among $Ar_1$ to $Ar_4$, the groups which are not represented by Formula (2) each are independently a substituted or non-substituted aryl group having 6 to 50 ring atoms; provided that substituents for $Ar_1$ to $Ar_4$ are a substituted or non-substituted aryl group having 6 to 50 ring atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 2 to 50 carbon atoms, a halogen atom, a cyano group, a nitro group, a hydroxy group or a carboxyl group.

In the aromatic amine derivative of the present invention, Formula (2) described above is preferably represented by Formula (3) shown below;

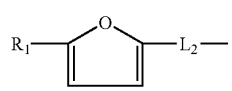
(3)

In Formula (3), $R_1$ is a substituted or non-substituted aryl group having 6 to 50 ring atoms or a substituted or non-substituted alkyl group having 1 to 50 carbon atoms; and $L_2$ represents a substituted or non-substituted arylene group having 6 to 50 ring atoms.

In the aromatic amine derivative of the present invention, $Ar_1$ in Formula (1) described above is preferably represented by Formula (2) described above.

Preferably, in the aromatic amine derivative of the present invention, $Ar_1$ and $Ar_2$ in Formula (1) described above each are independently represented by Formula (2) described above.

Preferably, in the aromatic amine derivative of the present invention, $Ar_1$ and $Ar_3$ in Formula (1) described above each are independently represented by Formula (2) described above.

In the aromatic amine derivative of the present invention, three or more of $Ar_1$ to $Ar_4$ in Formula (1) described above are preferably different from each other and the molecular structure of the aromatic amine compound is asymmetric.

In the aromatic amine derivative of the present invention, three of $Ar_1$ to $Ar_4$ in Formula (1) described above are preferably the same and the molecular structure of the aromatic amine compound is asymmetric.

Preferably, in the aromatic amine derivative of the present invention, $Ar_1$ to $Ar_4$ in Formula (1) described above each are independently phenyl, biphenyl, terphenyl or fluorenyl.

In the aromatic amine derivative of the present invention, $L_1$ in Formula (1) described above is preferably biphenylene, terphenylene or fluorenylene.

In the aromatic amine derivative of the present invention, $L_2$ in Formula (2) described above is preferably phenylene, biphenylene or fluorenylene.

In the aromatic amine derivative of the present invention, $R_1$ in Formula (2) described above is preferably phenyl, naphthyl or phenanthrene.

Preferably, in the aromatic amine derivative of the present invention, $Ar_1$ to $Ar_4$ in Formula (1) described above each are independently phenyl, biphenyl, terphenyl or fluorenyl; $L_1$ is biphenylene, terphenylene or fluorenylene; and $L_2$ in Formula (2) is phenylene, biphenylene or fluorenylene.

Further, the present invention provides an aromatic amine derivative represented by any of the following Formulas (4) to (6):

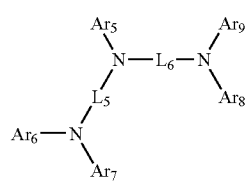
(4)

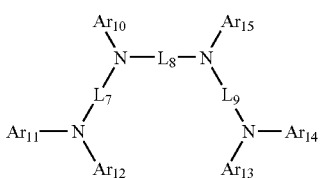
(5)

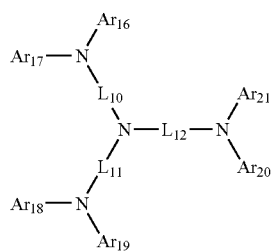
(6)

in Formulas (4) to (6), $L_5$ to $L_{12}$ represent a substituted or non-substituted arylene group having 6 to 50 ring atoms; at least one of $Ar_5$ to $Ar_9$ is represented by the following Formula (7); at least one of $Ar_{10}$ to $Ar_{15}$ is represented by the following Formula (7); and at least one of $Ar_{16}$ to $Ar_{21}$ is represented by the following Formula (7).

(7)

In Formula (7), $R_1$ is a hydrogen atom, a substituted or non-substituted aryl group having 6 to 50 ring atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 2 to 50 carbon atoms, a halogen atom, a cyano group, a nitro group, a hydroxy group or a carboxyl group; a is an integer of 0 to 3; and $L_2$ represents a substituted or non-substituted arylene group having 6 to 50 ring atoms.

In Formulas (4) to (6), $Ar_5$ to $Ar_{21}$ each are independently a substituted or non-substituted aryl group having 6 to 50 ring atoms; provided that substituents for $Ar_5$ to $Ar_{21}$ are a substituted or non-substituted aryl group having 6 to 50 ring atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 2 to 50 carbon atoms, a halogen atom, a cyano group, a nitro group, a hydroxy group or a carboxyl group.

In the aromatic amine derivative of the present invention, Formula (7) described above is preferably represented by Formula (8) shown below;

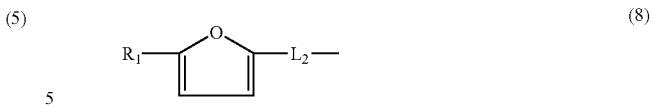
(8)

In Formula (8), $R_1$ is a substituted or non-substituted aryl group having 6 to 50 ring atoms or a substituted or non-substituted alkyl group having 1 to 50 carbon atoms; and $L_2$ represents a substituted or non-substituted arylene group having 6 to 50 ring atoms.

In the aromatic amine derivative of the present invention, at least one of $Ar_5$ to $Ar_9$ in Formula (4) described above is preferably represented by Formula (7).

In the aromatic amine derivative of the present invention, $Ar_5$ in Formula (4) described above is preferably represented by Formula (7) described above.

Preferably, in the aromatic amine derivative of the present invention, $Ar_6$ and $Ar_8$ in Formula (4) described above each are independently represented by Formula (7) described above.

In the aromatic amine derivative of the present invention, at least one of $Ar_{10}$ to $Ar_{15}$ in Formula (5) described above is preferably represented by Formula (7).

Preferably, in the aromatic amine derivative of the present invention, $Ar_{10}$ and $Ar_{15}$ in Formula (5) described above each are independently represented by Formula (7) described above.

Preferably, in the aromatic amine derivative of the present invention, $Ar_{11}$ and $Ar_{13}$ in Formula (5) described above each are independently represented by Formula (7) described above.

In the aromatic amine derivative of the present invention, at least one of $Ar_{16}$ to $Ar_{21}$ in Formula (6) described above is preferably represented by Formula (7).

Preferably, in the aromatic amine derivative of the present invention, $Ar_{16}$, $Ar_{18}$ and $Ar_{20}$ in Formula (6) described above each are independently represented by Formula (7) described above.

Preferably, in the aromatic amine derivative of the present invention, $Ar_5$ to $Ar_{21}$ in Formulas (4), (5) and (6) described above each are independently phenyl, biphenyl, terphenyl or fluorenyl.

Preferably, in the aromatic amine derivative of the present invention, $L_5$ to $L_{12}$ in Formulas (4), (5) and (6) described above each are independently phenylene, biphenylene, terphenylene or fluorenylene.

In the aromatic amine derivative of the present invention, $L_2$ in Formula (7) described above is preferably phenylene, biphenylene or fluorenylene.

In the aromatic amine derivative of the present invention, $R_1$ in Formula (7) described above is preferably phenyl, naphthyl or phenanthrene.

Preferably, in the aromatic amine derivative of the present invention, $Ar_5$ to $Ar_{21}$ in Formulas (4), (5), (6) and (7) described above each are independently phenyl, biphenyl, terphenyl or fluorenyl; $L_5$ to $L_{12}$ each are independently phenylene, biphenylene, terphenylene or fluorenylene; and $L_2$ is phenylene, biphenylene or fluorenylene.

Among $Ar_1$ to $Ar_4$ in Formula (1), a substituted or non-substituted aryl group having 6 to 50 ring atoms which is not represented by Formula (2), a substituted or non-substituted aryl group having 6 to 50 ring atoms represented by $R_1$ in Formulas (2), (3), (7) and (8) and a substituted or non-substituted aryl group having 6 to 50 ring atoms which is a substituent for $Ar_1$ to $Ar_4$ include, for example, phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, fluoranthenyl, fluorenyl and the like.

Among them, phenyl, naphthyl, biphenylyl, terphenylyl and fluorenyl are preferred.

The substituted or non-substituted arylene groups having 6 to 50 ring atoms represented by $L_1$ in Formulas (1), $L_2$ in Formulas (2), (3), (7) and (8) and $L_5$ to $L_{12}$ in Formulas (4) to (6) include groups obtained by converting the examples of the aryl group described above into divalent groups.

The substituted or non-substituted alkyl groups having 1 to 50 carbon atoms which are represented by $R_1$ in Formulas (2), (3), (7) and (8) and which are substituents for $Ar_1$ to $Ar_{21}$ in Formulas (1), (4), (5) and (6) include, for example, methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl, cyclopropyl, cyclobutyl, cyclopentyl, cyclohexyl, 4-methylcyclohexyl, 1-adamantyl, 2-adamantyl, 1-norbornyl, 2-norbornyl and the like.

The alkoxy groups having 1 to 50 carbon atoms which are represented by $R_1$ in Formulas (2) and (7) and which are substituents for $Ar_1$ to $Ar_{21}$ in Formulas (1), (4), (5) and (6) are groups represented by —OY, and the examples of Y include the same examples as explained in the alkyl groups described above.

The aralkyl groups having 6 to 50 carbon atoms which are represented by $R_1$ in Formulas (2) and (7) and which are substituents for $Ar_1$ to $Ar_{21}$ in Formulas (1), (4), (5) and (6) include, for example, benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, 1-chloro-2-phenylisopropyl and the like.

The aryloxy groups having 5 to 50 ring atoms which are represented by $R_1$ in Formulas (2) and (7) and which are substituents for $Ar_1$ to $Ar_{21}$ in Formulas (1), (4), (5) and (6) are represented by —OY', and the examples of Y' include the same examples as explained in the aryl groups described above.

The arylthio groups having 5 to 50 ring atoms which are represented by $R_1$ in Formulas (2) and (7) and which are substituents for $Ar_1$ to $Ar_{21}$ in Formulas (1), (4), (5) and (6) are represented by —SY', and the examples of Y' include the same examples as explained in the aryl groups described above.

The alkoxycarbonyl groups having 2 to 50 carbon atoms which are represented by $R_1$ in Formulas (2) and (7) and which are substituents for $Ar_1$ to $Ar_{21}$ in Formulas (1), (4), (5) and (6) are groups represented by —COOY, and the examples of Y include the same examples as explained in the alkyl groups described above.

The halogen atoms which are represented by $R_1$ in Formulas (2) and (7) and which are substituents for $Ar_1$ to $Ar_{21}$ in Formulas (1), (4), (5) and (6) include a fluorine atom, a chlorine atom, a bromine atom and an iodine atom.

In Formulas (2) and (7), a is an integer of 0 to 3.

The specific examples of the aromatic amine derivative of the present invention represented by Formula (1) are shown below, but they shall not be restricted to these compounds shown as the examples.

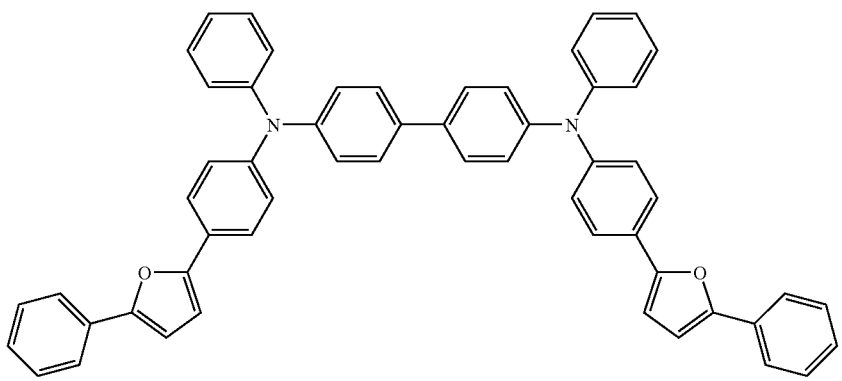

-continued
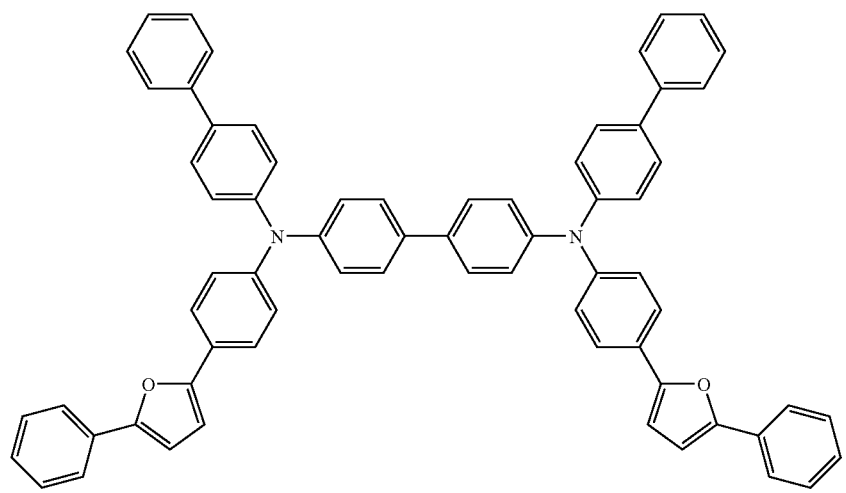
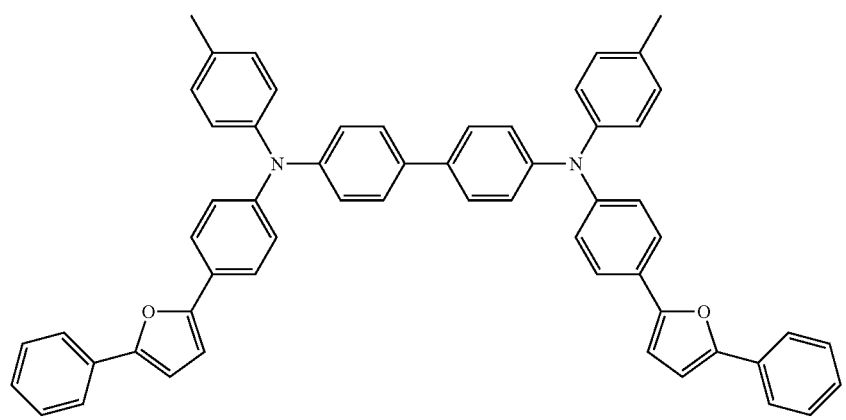
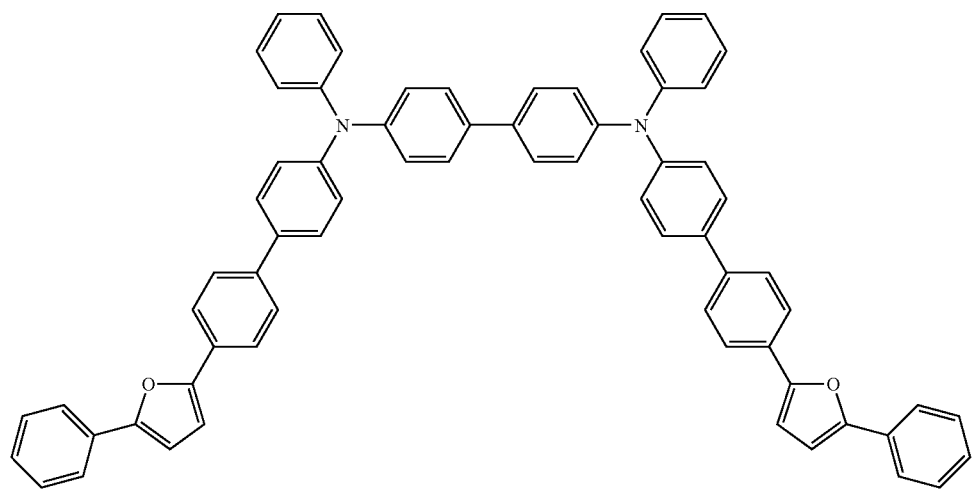

-continued
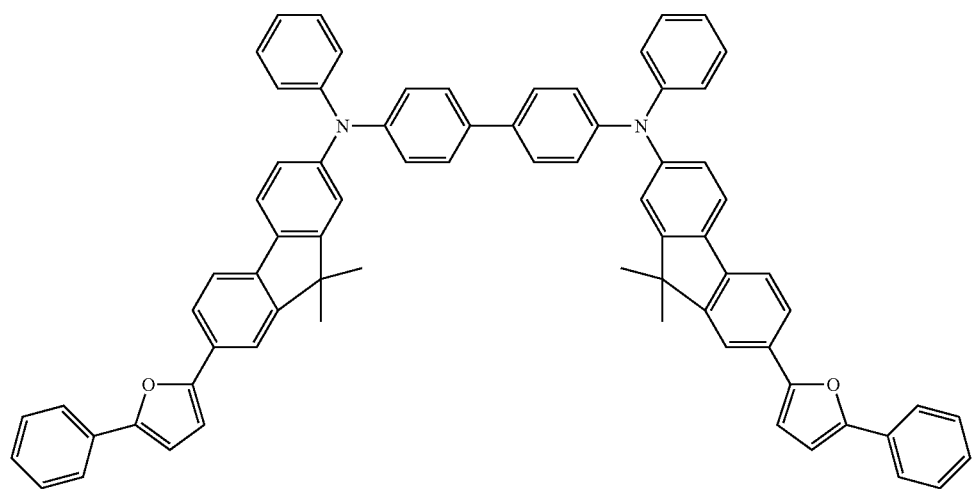
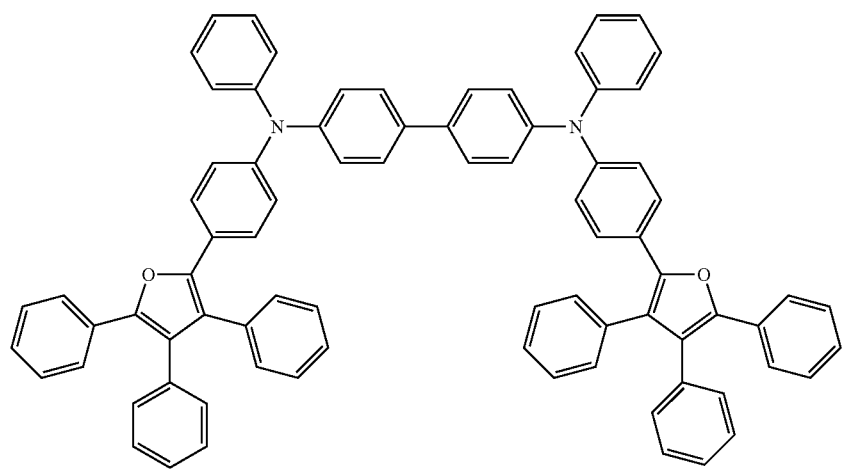
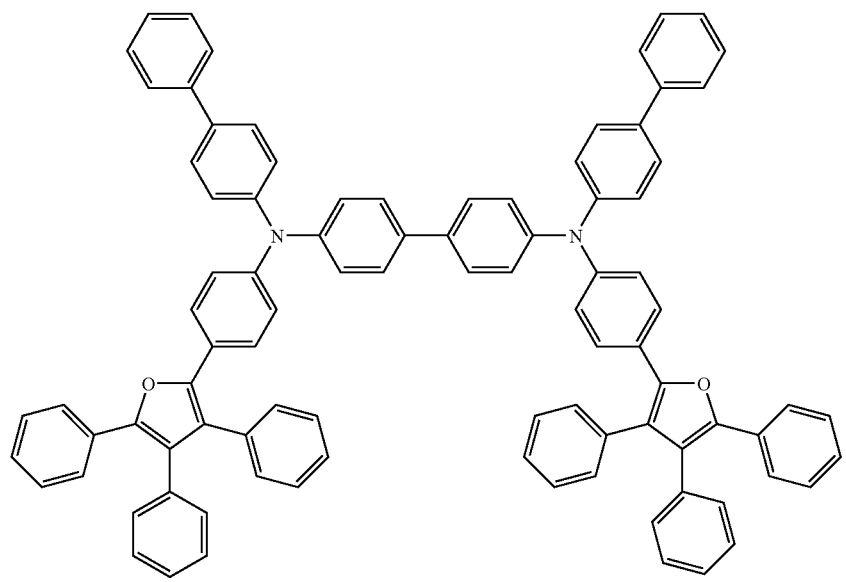

-continued
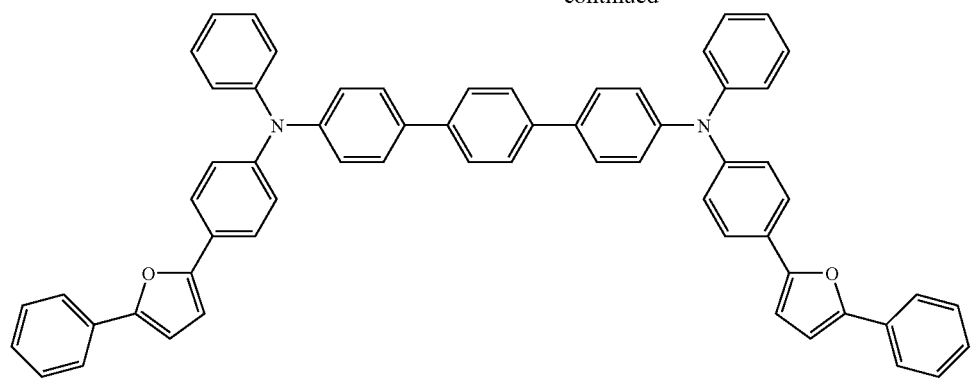
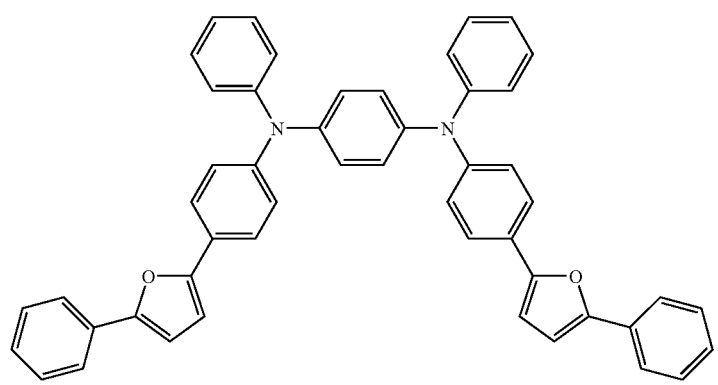
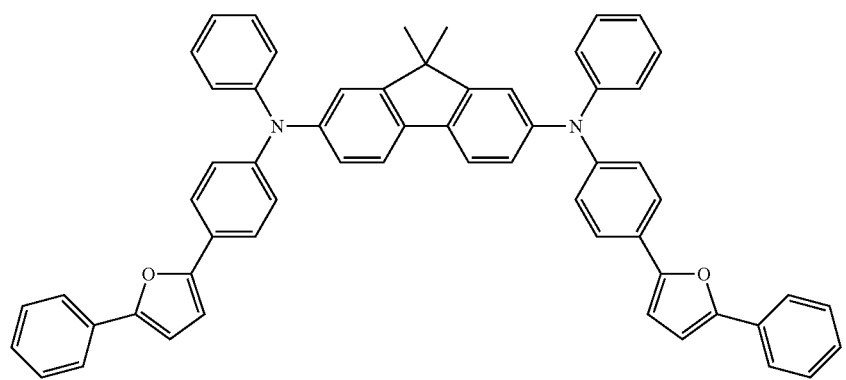
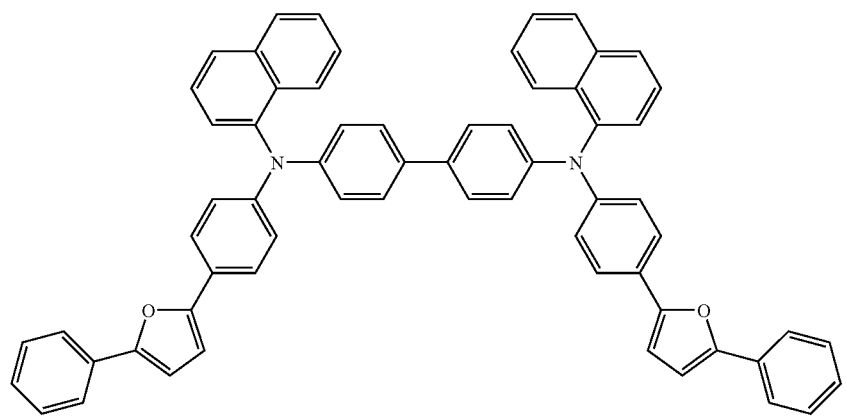

-continued
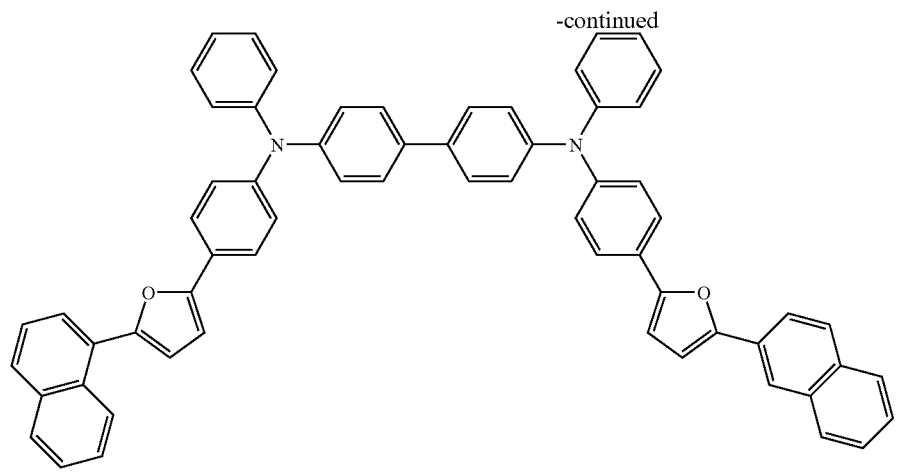
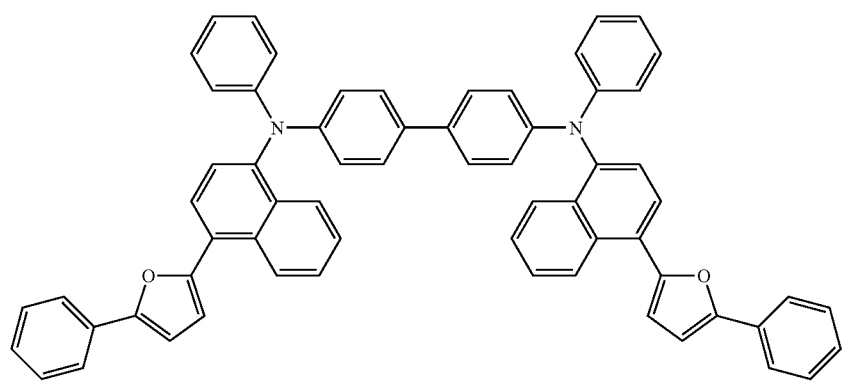
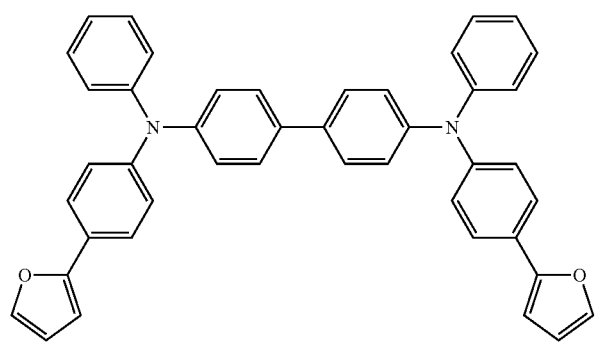
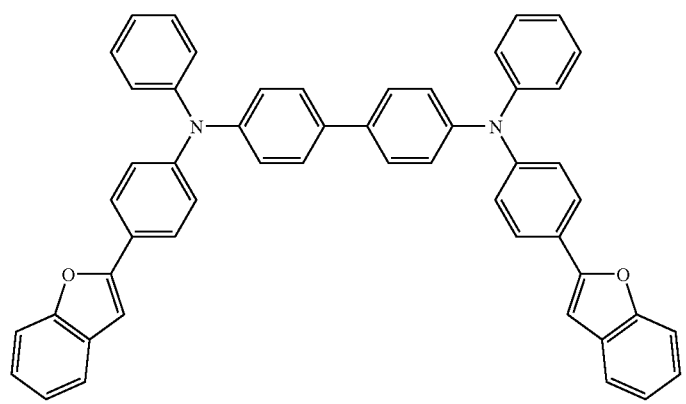

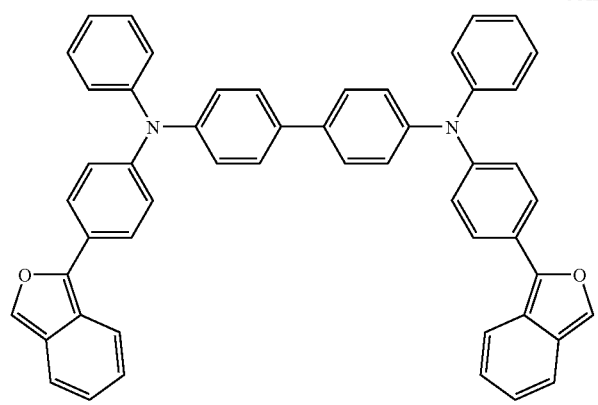
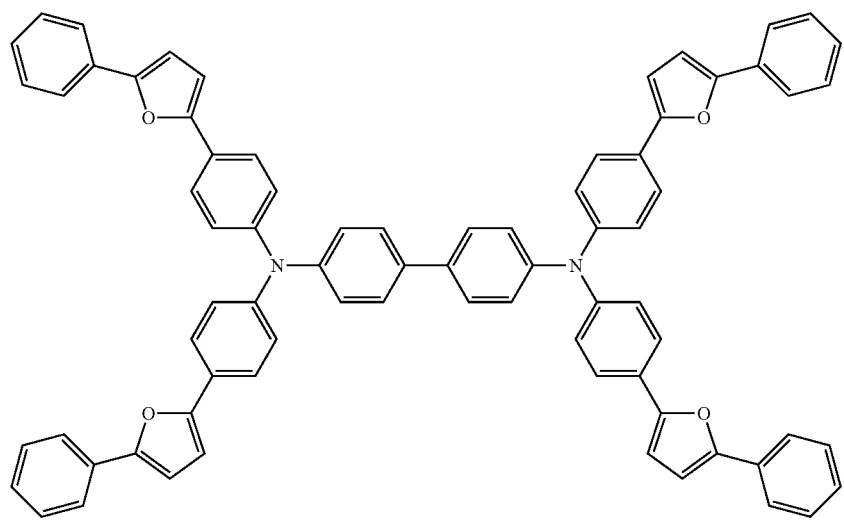
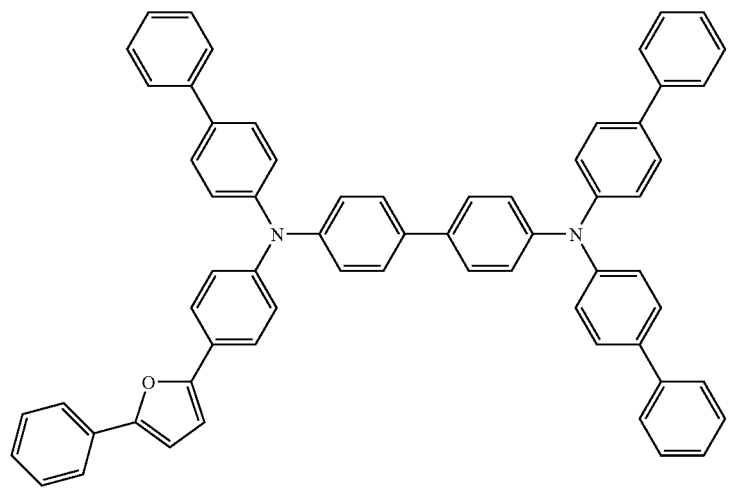

-continued
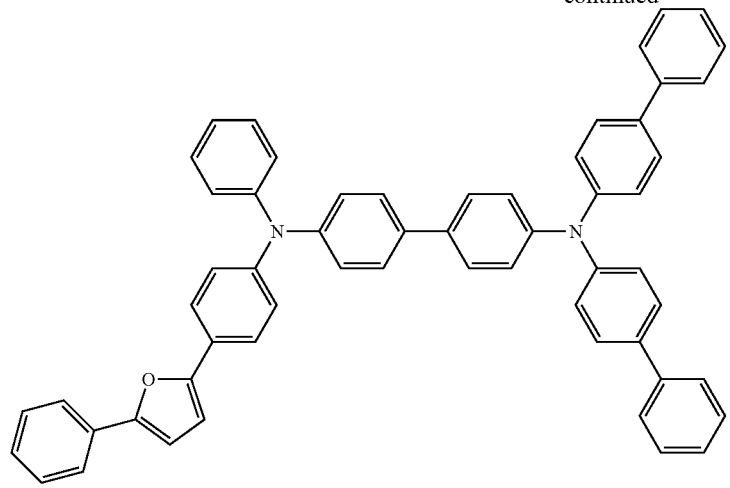
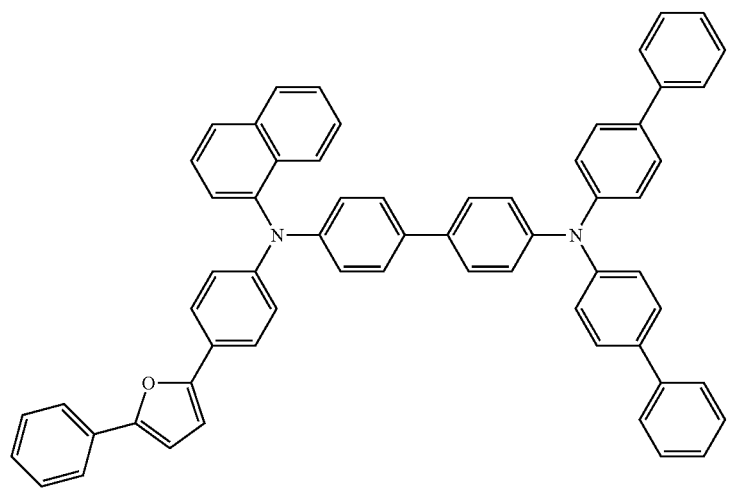
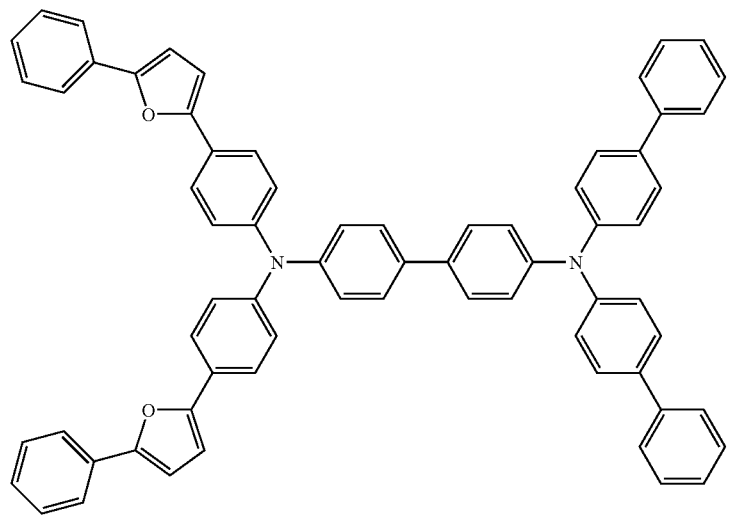

-continued
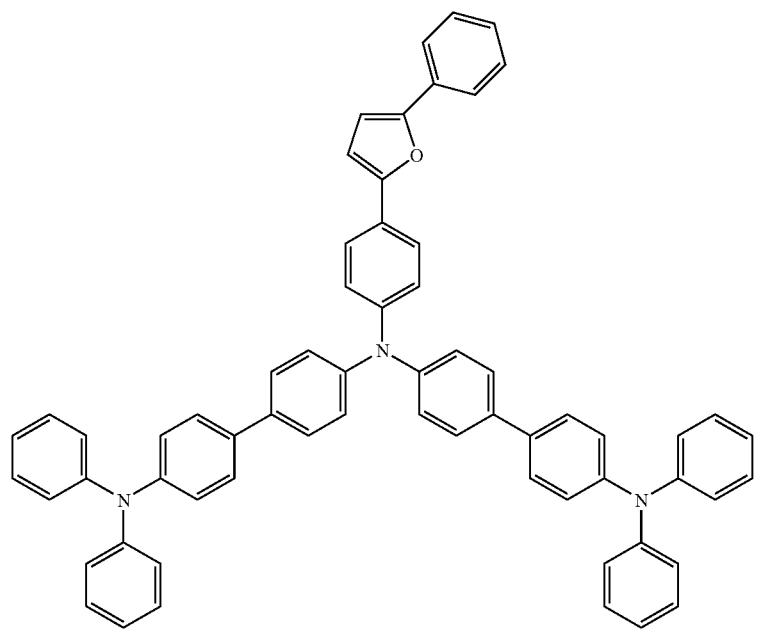
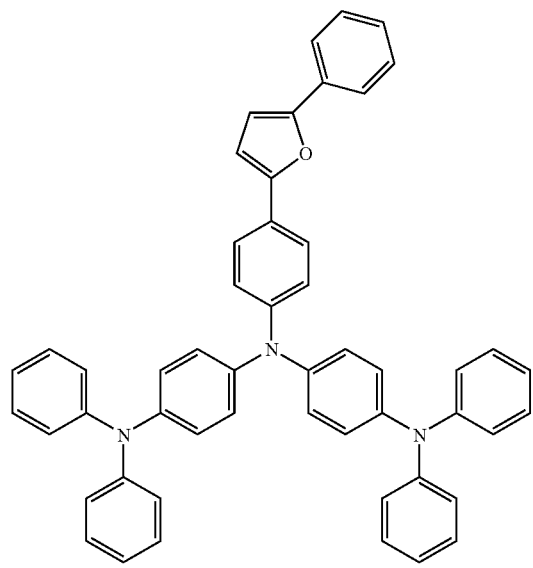

-continued
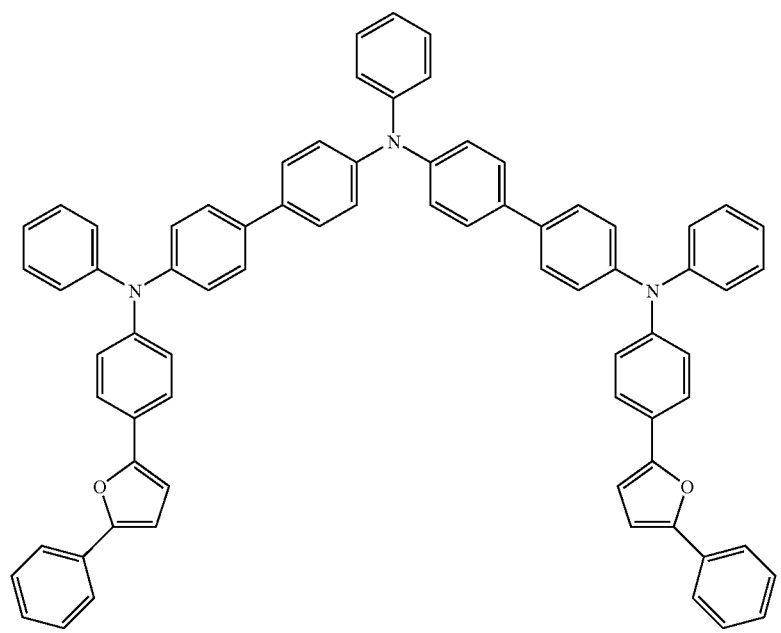
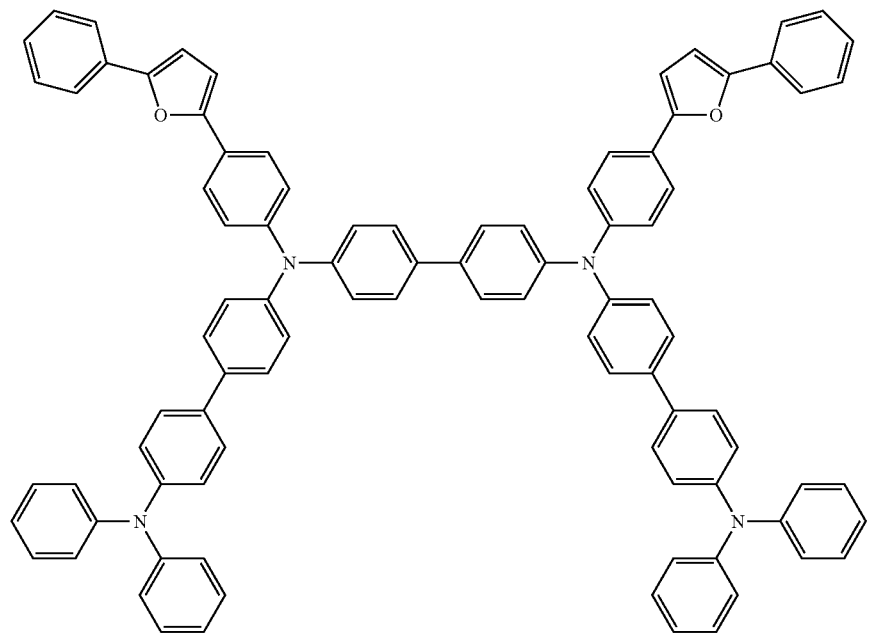

-continued
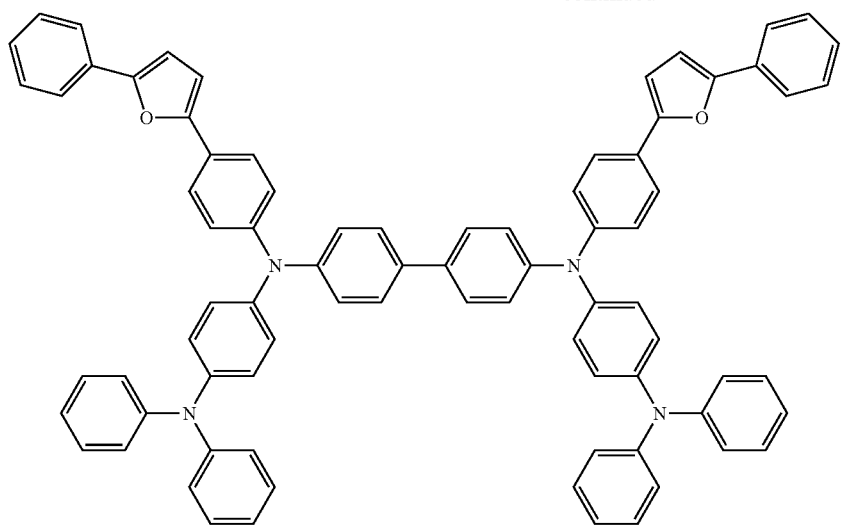
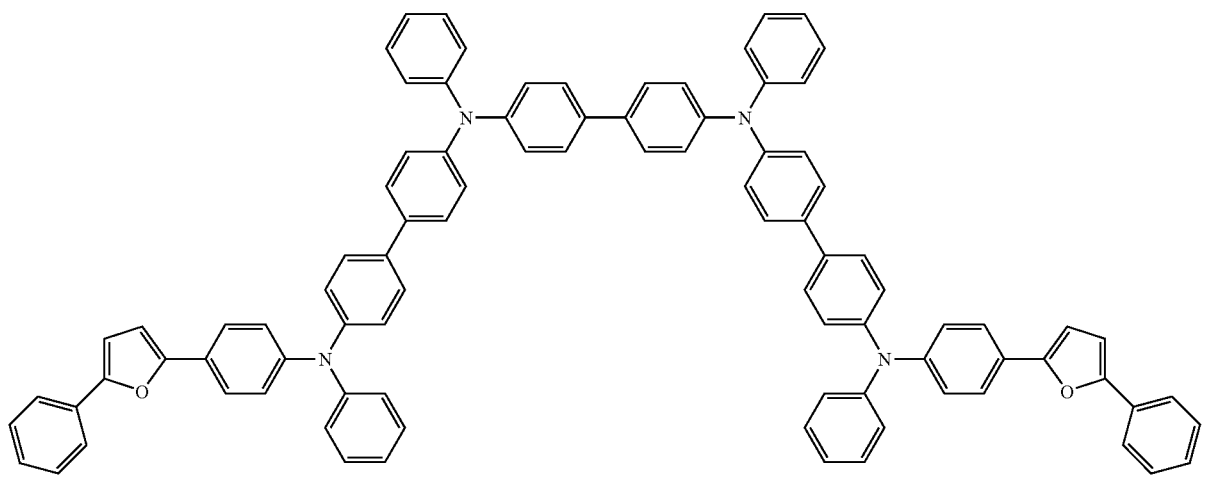
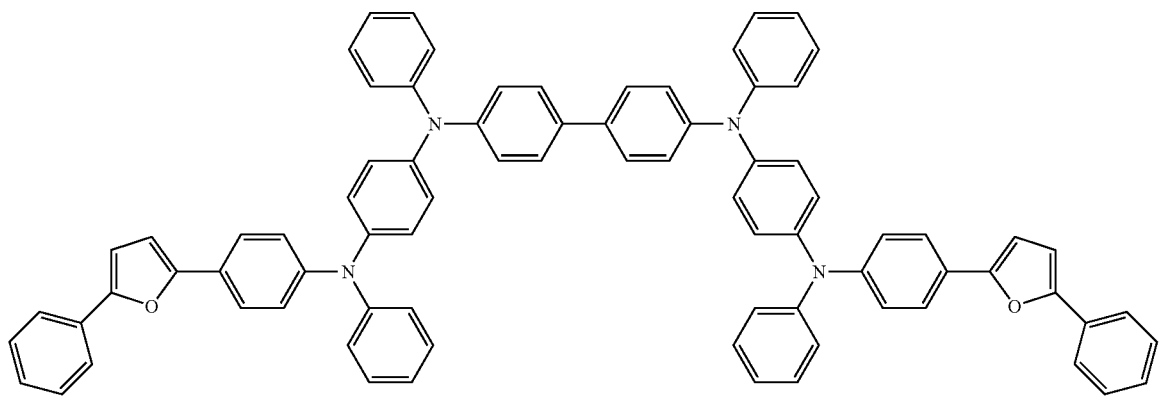

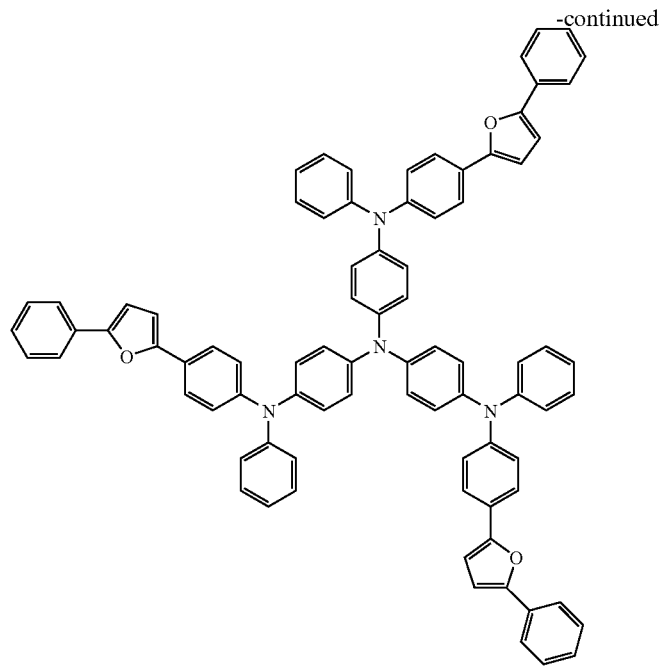

The aromatic amine derivative of the present invention is preferably a material for an organic electroluminescence device.

The aromatic amine derivative of the present invention is preferably a hole transporting material for an organic electroluminescence device.

Further, the present invention provides an organic EL device in which an organic thin layer comprising a single layer or plural layers including at least a light emitting layer is interposed between a cathode and an anode, wherein at leas one layer in the above organic thin layer contains the aromatic amine derivative described above in the form of a single component or a mixed component.

In the organic EL device of the present invention, the above organic thin film layer comprises a hole transporting layer, and the aromatic amine derivative described above is preferably contained in the above hole transporting layer.

In the organic EL device of the present invention, the above organic thin film layer comprises plural hole transporting layers, and the aromatic amine derivative described above is preferably contained in the transporting layer which is not brought into direct contact with the light emitting layer.

In the organic EL device of the present invention, the above organic thin film layer comprises a hole injecting layer, and the aromatic amine derivative described above is preferably contained in the above hole injecting layer.

In the organic EL device of the present invention, the aromatic amine derivative described above is preferably contained in the hole injecting layer as a main component.

A fluorescent dopant is preferably a compound selected according to a required light emitting color from amine base compounds, aromatic compounds, chelate complexes such as tris(8-quinolinolato) aluminum complex and the like, coumarin derivatives, tetraphenylbutadiene derivatives, bisstyrylarylene derivatives, oxadiazole derivatives and the like, and in particular, it includes arylamine compounds and styrylamine compounds. Among them, styrylamine compounds, styryldiamine compounds, aromatic amine compounds and aromatic diamine compounds are more preferred. Fused polycyclic aromatic compounds (excluding amine compounds) are further preferred. The above fluorescent dopants may be used alone or in combination of a plurality thereof.

The above styrylamine compounds and styryldiamine compounds are preferably compounds represented by the following Formula (A):

(A)

(wherein $Ar^3$ is a group selected from phenyl, naphthyl, biphenyl, terphenyl, stilbene and distyrylaryl; $Ar^4$ and $Ar^5$ each are an aromatic hydrocarbon group having 6 to 20 carbon atoms, and $Ar^3$, $Ar^4$ and $Ar^5$ may be substituted; p is an integer of 1 to 4, and among them, p is preferably an integer of 1 to 2; any one of $Ar^3$ to $Ar^5$ is a group containing a styryl group; and at least one of $Ar^4$ and $Ar^5$ is substituted with a styryl group).

In this regard, the aromatic hydrocarbon group having 6 to 20 carbon atoms includes phenyl, naphthyl, anthracenyl, phenanthryl, terphenyl and the like.

The aromatic amine compound and the aromatic diamine compound are preferably compounds represented by the following Formula (B):

(B)

(wherein $Ar^6$ to $Ar^8$ are a substituted or non-substituted aryl group having 5 to 40 ring carbon atoms; q is an integer of 1 to 4, and among them, q is preferably an integer of 1 to 2).

In this regard, the aryl group having 5 to 40 ring carbon atoms includes, for example, phenyl, naphthyl, anthracenyl, phenanthryl, pyrenyl, coronyl, biphenyl, terphenyl, pyrrolyl, furanyl, thiophenyl, benzothiophenyl, oxadiazolyl, diphenylanthracenyl, indolyl, carbazolyl, pyridyl, benzoquinolyl, fluoranthenyl, acenaphthofluoranthenyl, stilbene, perylenyl, chrysenyl, picenyl, triphenylenyl, rubicenyl, benzoanthracenyl, phenylanthracenyl, bisanthracenyl or aryl groups represented by the following Formulas (C) and (D), and naphthyl, anthranyl, chrysenyl, pyrenyl and an aryl group represented by Formula (D) are preferred.

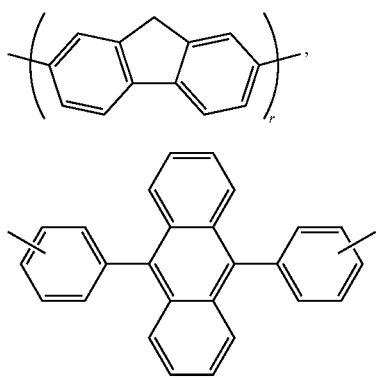

(in Formula (C), r is an integer of 1 to 3).

Preferred substituents with which the aryl group described above is substituted include an alkyl group having 1 to 6 carbon atoms (ethyl, methyl, i-propyl, n-propyl, s-butyl, t-butyl, pentyl, hexyl, cyclopentyl, cyclohexyl and the like), an alkoxy group having 1 to 6 carbon atoms (ethoxy, methoxy, i-propoxy, n-propoxy, s-butoxy, t-butoxy, pentoxy, hexyloxy, cyclopentoxy, cyclohexyloxy and the like), an aryl group having 5 to 40 ring carbon atoms, an amino group substituted with an aryl group having 5 to 40 ring carbon atoms, an ester group having an aryl group having 5 to 40 ring carbon atoms, an ester group having an alkyl group having 1 to 6 carbon atoms, a cyano group, a nitro group, a halogen atom and the like.

The fused polycyclic aromatic compounds (excluding amine compounds) are preferably fused polycyclic aromatic compounds such as naphthalene, anthracene, phenanthrene, pyrene, coronene, biphenyl, terphenyl, pyrrole, furan, thiophene, benzothiophene, oxadiazole, indole, carbazole, pyridine, benzoquinoline, fluoranthenine, benzofluoranthene, acenaphthofluoranthenine, stilbene, perylene, chrysene, picene, triphenylenine, rubicene, benzoanthracene and the like and derivatives thereof.

In the aromatic amine derivative of the present invention, a layer brought into contact with the anode which is present in the hole injecting layer described above is preferably a layer containing an acceptor material.

The aromatic amine derivative of the present invention is used preferably for an organic EL device which emits light of a blue color.

The device structure of the organic EL device of the present invention shall be explained below.
(1) Structure of the Organic EL Device The typical examples of the device structure of the organic EL device of the present invention include structures such as:
(1) Anode/light emitting layer/cathode
(2) Anode/hole injecting layer/light emitting layer/cathode
(3) Anode/light emitting layer/electron injecting layer/cathode
(4) Anode/hole injecting layer/light emitting layer/electron injecting layer/cathode
(5) Anode/organic semiconductor layer/light emitting layer/cathode
(6) Anode/organic semiconductor layer/electron barrier layer/light emitting layer/cathode
(7) Anode/organic semiconductor layer/light emitting layer/adhesion improving layer/cathode
(8) Anode/hole injecting layer/hole transporting layer/light emitting layer/electron injecting layer/cathode
(9) Anode/acceptor containing layer/hole injecting layer/hole transporting layer/light emitting layer/electron transporting layer/electron injecting layer/cathode
(10) Anode/insulating layer/light emitting layer/insulating layer/cathode
(11) Anode/inorganic semiconductor layer/insulating layer/light emitting layer/insulating layer/cathode
(12) Anode/organic semiconductor layer/insulating layer/light emitting layer/insulating layer/cathode
(13) Anode/insulating layer/hole injecting layer/hole transporting layer/light emitting layer/insulating layer/cathode
(14) Anode/insulating layer/hole injecting layer/hole transporting layer/light emitting layer/electron injecting layer/cathode Among them, usually the structure of (8) is preferably used, but it shall not be restricted to them.

The aromatic amine derivative of the present invention may be used in any organic thin film layers of the organic EL device and can be used in the light emitting zone or the hole transporting zone, and it is used preferably in the hole transporting zone, particularly preferably in the hole injecting layer, whereby the molecules are less liable to be crystallized, and a yield in producing the organic EL device is enhanced.

An amount of the aromatic amine derivative of the present invention added to the organic thin film layer is preferably 30 to 100 mole %.
(2) Light Transmitting Substrate The organic EL device of the present invention is prepared on a light transmitting substrate. The light transmitting substrate referred to in this case is a substrate for supporting the organic EL device, and it is preferably a flat substrate in which light in a visible region of 400 to 700 nm has a light transmittance of 50% or more.

To be specific, it includes a glass plate, a polymer plate and the like. In particular, the glass plate includes soda lime glass, barium-strontium-containing glass, lead glass, aluminosilicate glass, borosilicate glass, barium borosilicate glass, quartz and the like. The polymer plate includes polycarbonate, acryl, polyethylene terephthalate, polyether sulfide, polysulfone and the like.
(3) Anode An anode in the organic EL device of the present invention has a function to inject a hole into the hole transporting layer or the light emitting layer, and it is effective that the anode has a work function of 4.5 eV or more. The specific examples of a material for the anode used in the present invention include indium tin oxide alloy (ITO), tin oxide (NESA), indium-zinc oxide (IZO), gold, silver, platinum, copper and the like.

The anode can be prepared by forming a thin film from the above electrode substances by a method such as a vapor deposition method, a sputtering method and the like.

When light emitted from the light emitting layer is taken out from the anode, a light transmittance of the anode based on light emitted is preferably larger than 10%. The anode has a sheet resistance of preferably several hundred Ω/□ or less.

A film thickness of the anode is selected, though depending on the material, in a range of usually 10 nm to 1 μm, preferably 10 to 200 nm.

(4) Light Emitting Layer

The light emitting layer in the organic EL device has the following functions of (1) to (3) in combination.

(1) Injecting function: a function in which a hole can be injected from an anode or a hole injecting layer in applying an electric field and in which an electron can be injected from a cathode or an electron injecting layer.

(2) Transporting function: a function in which a charge (electron and hole) injected is transferred by virtue of a force of an electric field.

(3) Light emitting function: a function in which a field for recombination of an electron and a hole is provided and in which this is connected to light emission.

Provided that a difference between an easiness in injection of a hole and an easiness in injection of an electron may be present and that a difference may be present in a transporting ability shown by the mobilities of a hole and an electron, and any one of the charges is preferably transferred.

A publicly known method such as, for example, a vapor deposition method, a spin coating method, an LB method and the like can be applied as a method for forming the above light emitting layer. In particular, the light emitting layer is preferably a molecular deposit film. In this case, the molecular deposit film means a thin film formed by depositing a material compound staying in a gas phase state or a film formed by solidifying a material compound staying in a solution state or a liquid phase state, and the above molecular deposit film can usually be distinguished from a thin film (molecular accumulation film) formed by the LB method by a difference in an aggregation structure and a higher order structure and a functional difference originating in it.

Further, as disclosed in Japanese Patent Application Laid-Open No. 51781/1982, the light emitting layer can be formed as well by dissolving a binding agent such as a resin and the material compound in a solvent to prepare a solution and then coating the solution by a spin coating method and the like to form a thin film.

When the compound of the present invention is used for the light emitting layer, other publicly known light emitting materials excluding the light emitting material comprising the aromatic amine derivative of the present invention may be added, if necessary, to the light emitting layer as long as the object of the present invention is not damaged. Further, a light emitting layer containing a different publicly known light emitting material may be laminated on the light emitting layer containing the light emitting material comprising the aromatic amine derivative of the present invention.

A light emitting material used in combination with the compound of the present invention is mainly an organic compound, and a doping material which can be used includes, for example, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bis-styryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxynoid compounds, quinacridone, rubrene, fluorescent coloring matters and the like. However, it shall not be restricted to them.

The host material which can be used in combination with the compound of the present invention is preferably compounds represented by the following Formulas (i) to (xi).

Asymmetric anthracene represented by the following Formula (1):

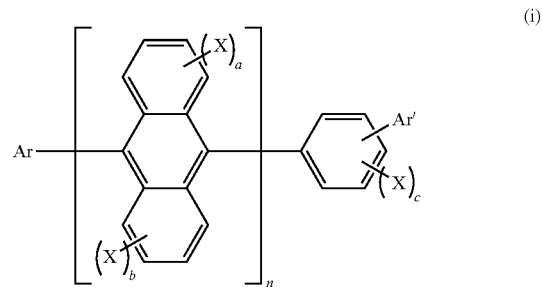

(wherein Ar is a substituted or non-substituted fused aromatic group having 10 to 50 ring carbon atoms;

Ar' is a substituted or non-substituted aromatic group having 6 to 50 ring carbon atoms;

X is a substituted or non-substituted aromatic group having 6 to 50 ring carbon atoms, a substituted or non-substituted aromatic heterocyclic group having 5 to 50 ring atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, a carboxyl group, a halogen atom, a cyano group, a nitro group or a hydroxy group;

a, b and c each are an integer of 0 to 4;

n is an integer of 1 to 3; and when n is 2 or more, an inside of the brackets may be the same or different).

Asymmetric monoanthracene derivative represented by the following Formula (ii):

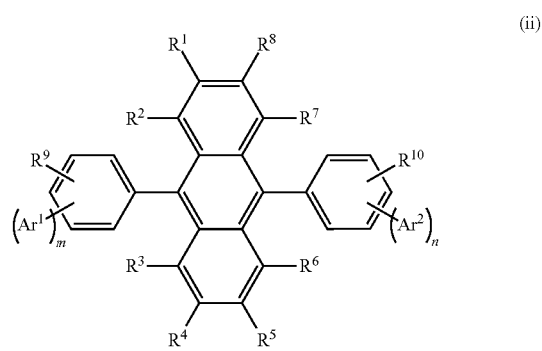

(wherein $Ar^1$ and $Ar^2$ each are independently a substituted or non-substituted aromatic ring group having 6 to 50 ring carbon atoms; m and n each are an integer of 1 to 4; provided that when m and n are 1 and the positions of $Ar^1$ and $Ar^2$ bonded to the benzene ring are bilaterally symmetric, $Ar^1$ and $Ar^2$ are not the same, and when m and n are an integer of 2 to 4, m and n are different integers; and $R^1$ to $R^{10}$ each are independently a hydrogen atom, a substituted or non-substituted aromatic ring group having 6 to 50 ring carbon atoms, a substituted or non-substituted aromatic heterocyclic group having 5 to 50 ring atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, a substituted or non-substituted silyl group, a carboxyl group, a halogen atom, a cyano group, a nitro group or a hydroxy group).

Asymmetric pyrene derivative represented by the following Formula (iii):

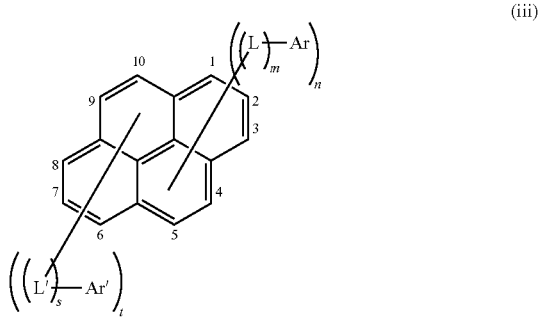

(iii)

[wherein Ar and Ar' each are a substituted or non-substituted aromatic group having 6 to 50 ring carbon atoms;
L and L' each are a substituted or non-substituted phenylene group, a substituted or non-substituted naphthalenylene group, a substituted or non-substituted fluorenylene group or a substituted or non-substituted dibenzosilolylene group;
m is an integer of 0 to 2; n is an integer of 1 to 4; s is an integer of 0 to 2; and t is an integer of 0 to 4;
L or Ar is bonded to any of 1- to 5-positions of pyrene, and L' or Ar' is bonded to any of 6- to 10-positions of pyrene;
provided that when n+t is an even number, Ar, Ar', L and L' satisfy (1) or (2) described below:
(1) Ar≠Ar' and/or L≠L' (in this case, ≠ shows that both are groups having different structures) and
(2) when Ar=Ar' and L=L',
  (2-1) m≠s and/or n≠t or
  (2-2) when m=s and n=t,
there are not a case in which (2-2-1) L and L' or pyrene each are bonded to different bonding positions on Ar and Ar' or (2-2-2) L and L' or pyrene are bonded to the same bonding position on Ar and Ar' and a case in which the substitution positions of L and L' or Ar and Ar' in pyrene are a 1-position and a 6-position or a 2-position and a 7-position].

Asymmetric anthracene derivative represented by the following Formula (iv):

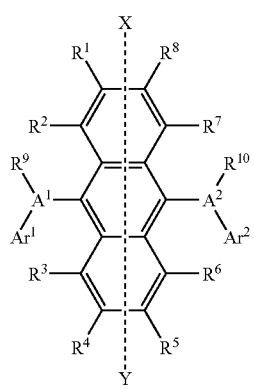

(iv)

(wherein $A^1$ and $A^2$ each are independently a substituted or non-substituted fused aromatic ring group having 10 to 20 ring carbon atoms;
$Ar^1$ and $Ar^2$ each are independently a hydrogen atom or a substituted or non-substituted aromatic ring group having 6 to 50 ring carbon atoms;
$R^1$ to $R^{10}$ each are independently a hydrogen atom, a substituted or non-substituted aromatic ring group having 6 to 50 ring carbon ring atoms, a substituted or non-substituted aromatic heterocyclic group having 5 to 50 ring atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, a substituted or non-substituted silyl group, a carboxyl group, a halogen atom, a cyano group, a nitro group or a hydroxy group;
$Ar_1$, $Ar^2$, $R^9$ and $R^{10}$ each may be plural, and the adjacent groups may form a saturated or unsaturated cyclic structure;
provided that there is no case in which in Formula (1), the groups symmetric to an X-Y axis shown on anthracene are bonded to a 9-position and a 10-position of the above anthracene in a center).

Anthracene derivative represented by the following Formula (v):

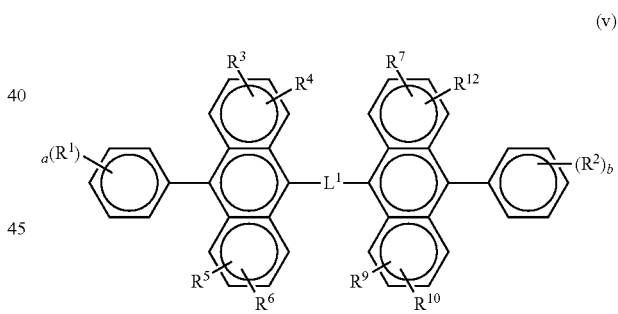

(v)

(wherein $R^1$ to $R^{10}$ each represent independently a hydrogen atom, an alkyl group, a cycloalkyl group, an aryl group which may be substituted, an alkoxyl group, an aryloxy group, an alkylamino group, an alkenyl group, an arylamino group or a heterocyclic group which may be substituted; a and b each represent an integer of 1 to 5; when they are 2 or more, $R^1$'s themselves or $R^2$'s themselves may be the same as or different from each other, and $R^1$'s themselves or $R^2$'s themselves may be combined with each other to form a ring; $R^3$ and $R^4$, $R^5$ and $R^6$, $R^7$ and $R^8$ and $R^9$ and $R^{10}$ may be combined with each other to form rings; and $L^1$ represents a single bond, —O—, —S—, —N(R)— (R is an alkyl group or an aryl group which may be substituted), an alkylene group or an arylene group).

Anthracene derivative represented by the following Formula (vi):

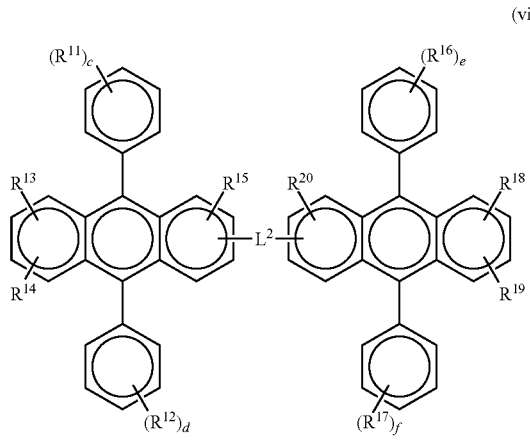

(vi)

(wherein $R^{11}$ to $R^{20}$ each represent independently a hydrogen atom, an alkyl group, a cycloalkyl group, an aryl group, an alkoxyl group, an aryloxy group, an alkylamino group, an arylamino group or a heterocyclic group which may be substituted; c, d, e and f each represent an integer of 1 to 5; when they are 2 or more, $R^{11}$'s themselves, $R^{12}$'s themselves, $R^{16}$'s themselves or $R^{17}$'s themselves may be the same as or different from each other, and $R^{11}$'s themselves, $R^{12}$'s themselves, $R^{16}$'s themselves or $R^{17}$'s themselves may be combined with each other to form a ring; $R^{13}$ and $R^{14}$ and $R^{18}$ and $R^{19}$ may be combined with each other to form rings; and $L^2$ represents a single bond, —O—, —S—, —N(R)— (R is an alkyl group or an aryl group which may be substituted), an alkylene group or an arylene group).

Spirofluorene derivative represented by the following Formula (vii):

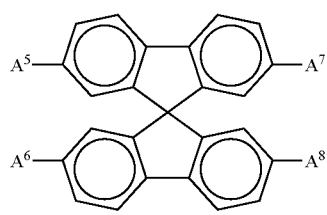

(vii)

(wherein $A^5$ to $A^8$ each are independently a substituted or non-substituted biphenylyl group or a substituted or non-substituted naphthyl group).

Fused ring-containing compound represented by the following Formula (viii):

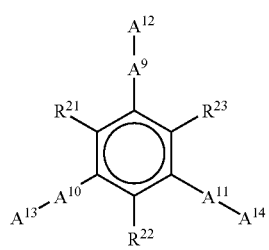

(viii)

(wherein $A^9$ to $A^{14}$ are the same as those described above; $R^{21}$ to $R^{23}$ each represent independently a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms or a halogen atom; and at least one of $A^9$ to $A^{14}$ is a group having 3 or more fused aromatic rings).

Fluorene compound represented by the following Formula (ix):

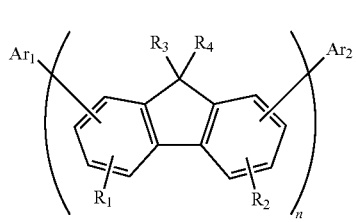

(ix)

(wherein $R_1$ and $R_2$ represent a hydrogen atom, a substituted or non-substituted alkyl group, a substituted or non-substituted aralkyl group, a substituted or non-substituted aryl group, a substituted or non-substituted heterocyclic group, a substituted amino group, a cyano group or a halogen atom; $R_1$'s themselves and $R_2$'s themselves which are bonded to the different fluorene groups may be the same as or different from each other, and $R_1$ and $R_2$ which are bonded to the same fluorene group may be the same or different; $R_3$ and $R_4$ represent a hydrogen atom, a substituted or non-substituted alkyl group, a substituted or non-substituted aralkyl group, a substituted or non-substituted aryl group or a substituted or non-substituted heterocyclic group; $R_3$'s themselves and $R_4$'s themselves which are bonded to the different fluorene groups may be the same as or different from each other, and $R_3$ and $R_4$ which are bonded to the same fluorene group may be the same or different; $Ar_1$ and $Ar_2$ represent a substituted or non-substituted fused polycyclic aromatic group in which the total of benzene rings is 3 or more or a fused polycyclic heterocyclic group in which the total of benzene rings and heterocycles is 3 or more and which is bonded to a fluorene group via substituted or non-substituted carbon; $Ar_1$ and $Ar_2$ may be the same or different; and n represents an integer of 1 to 10).

Compound having an anthracene central skeleton represented by the following Formula (x):

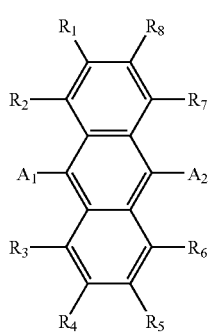

(x)

(in Formula (x), $A_1$ and $A_2$ each are independently a group derived from a substituted or non-substituted aromatic ring having 6 to 20 ring carbon atoms; the aromatic ring described above may be substituted with at least one substituent; the substituent described above is selected from a substituted or non-substituted aryl group having 6 to 50 ring carbon atoms, a substituted or non-substituted alkyl group having 1 to 50 carbon atoms, a substituted or non-substituted cycloalkyl group having 3 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, a substituted or non-substituted silyl group, a carboxyl group, a halogen atom, a cyano group, a nitro group and a hydroxyl group;

when the aromatic ring described above is substituted with two or more substituents, the substituents described above may be the same or different, and the adjacent substituents may be bonded with each other to form a saturated or unsaturated cyclic structure;

$R_1$ to $R_8$ each are independently selected from a hydrogen atom, a substituted or non-substituted aryl group having 6 to 50 ring carbon atoms, a substituted or non-substituted heteroaryl group having 5 to 50 ring atoms, a substituted or non-substituted alkyl group having 1 to 50 carbon atoms, a substituted or non-substituted cycloalkyl group having 3 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, a substituted or non-substituted silyl group, a carboxyl group, a halogen atom, a cyano group, a nitro group and a hydroxyl group).

Compound having a structure represented by the following Formula (xi) in which $A_1$ is different from $A_2$ in Formula (x) described above:

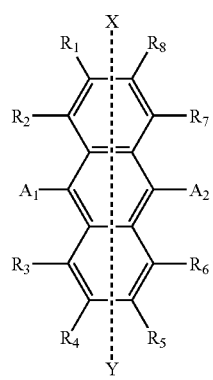

(xi)

(in Formula (xi), $A_1$, $A_2$ and $R_1$ to $R_8$ each are independently the same as in Formula (x); provided that a case in which the groups symmetric to an X-Y axis shown on anthracene are bonded to a 9-position and a 10-position of the above anthracene in a center is not present).

Among the host materials described above, the anthracene derivatives are preferred; the monoanthracene derivatives are more preferred; and the asymmetric anthracenes are particularly preferred.

The host suited to phosphorescence comprising the compound containing a carbazole ring is a compound having a function in which transfer of energy from an excited state thereof to a phosphorescent compound takes place to result in allowing the phosphorescent compound to emit light. The host compound shall not specifically be restricted as long as it is a compound which can transfer exciton energy to the phosphorescent compound, and it can suitably be selected according to the purposes. It may have an optional heterocycle in addition to a carbazole ring.

The specific examples of the above host compound include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene base compounds, porphyrin base compounds, anthraquinodimethane derivatives, anthrone derivatives, diphenylquinone derivatives, thiopyran dioxide derivatives, carbodiimide derivatives, fluorenilidenemethane derivatives, distyrylpyrazine derivatives, heterocyclic tetracarboxylic anhydride such as naphthaleneperylene and the like, phthalocyanine derivatives, metal complexes of 8-quinolinol derivatives, various metal complex polysilane base compounds represented by metal complexes comprising metal phthalocyanine, benzoxazole and benzothiazole as ligands, and high molecular compounds including poly(N-vinylcarbazole) derivatives, aniline base copolymers, thiophene oligomers, electroconductive high molecular oligomers such as polythiophene, polythiophene derivatives, polyphenylene derivatives, polyphenylenevinylene derivatives and polyfluorene derivatives. The host compounds may be used alone or in combination two or more kinds thereof.

The specific examples thereof include the following compounds:

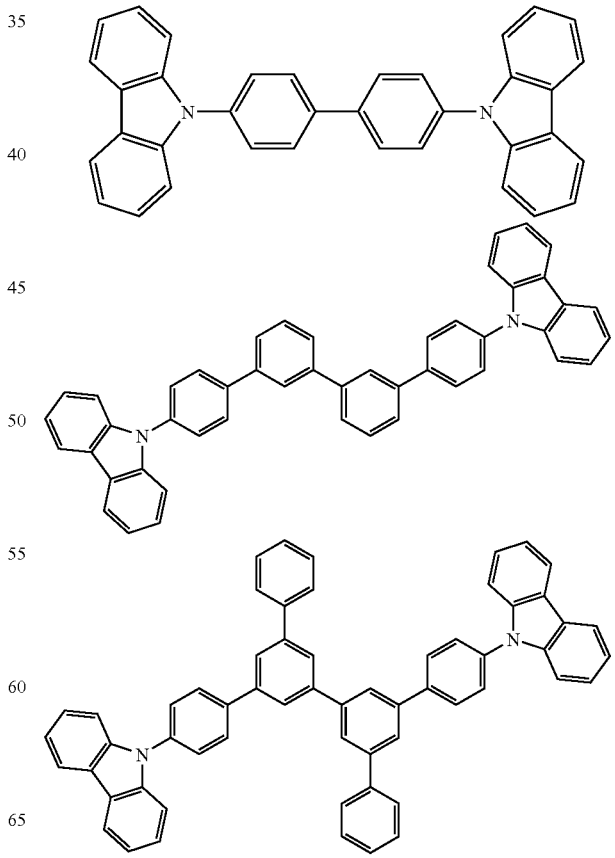

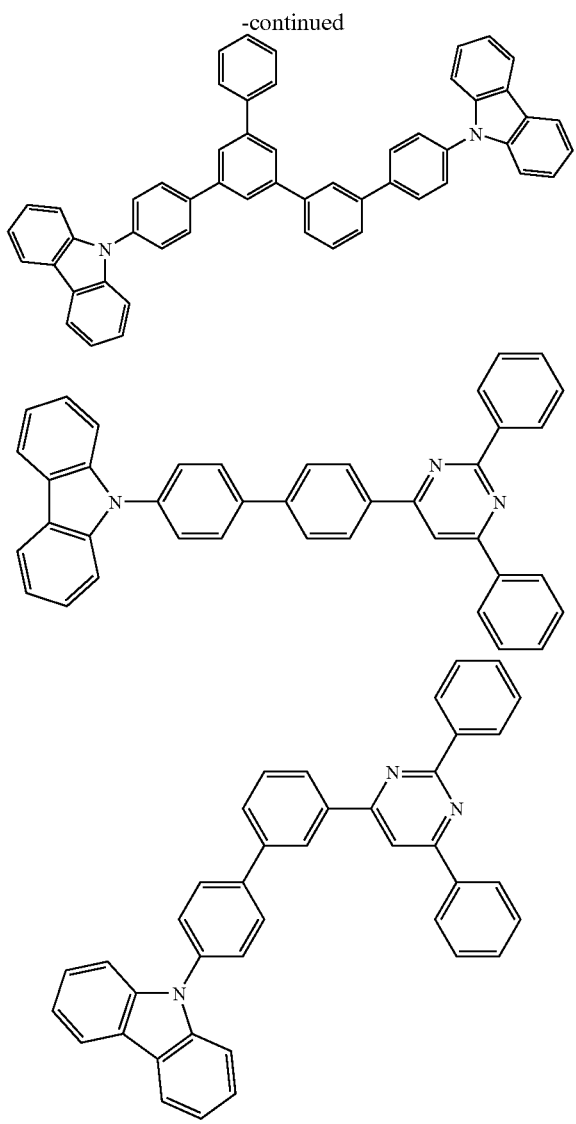

The phosphorescent dopant is a compound which can emit light from a triplet exciton. It shall not specifically be restricted as long as it emits light from a triplet exciton. It is preferably a metal complex containing at least one metal selected from the group consisting of Ir, Ru, Pd, Pt, Os and Re, and a porphyrin metal complex or an ortho-metallated metal complex is preferred. The porphyrin metal complex is preferably a porphyrin platinum complex. The phosphorescent compounds may be used alone or in combination of two or more kinds thereof.

A ligand forming the ortho-metallated metal complex includes various ones, and the preferred ligand includes 2-phenylpyridine derivatives, 7,8-benzoquinoline derivatives, 2-(2-thienyl)pyridine derivatives, 2-(1-naphthyl)pyridine derivatives, 2-phenylquinoline derivatives and the like. The above derivatives may have, if necessary, substituents. In particular, the compounds into which fluorides and trifluoromethyl are introduced are preferred as a blue color dopant. Further, it may have, as an auxiliary ligand, ligands other than the ligands described above such as acetylacetonate, picric acid and the like.

A content of the phosphorescent dopant in the light emitting layer shall not specifically be restricted, and it can suitably be selected according to the purposes. It is, for example, 0.1 to 70 mass %, preferably 1 to 30 mass %. If a content of the phosphorescent dopant is less than 0.1 mass %, light emission is faint, and an addition effect thereof is not sufficiently exhibited. On the other hand, if it exceeds 70 mass %, a phenomenon called concentration quenching is markedly brought about, and the device performance is reduced.

The light emitting layer may contain, if necessary, a hole transporting material, an electron transporting material and a polymer binder.

Further, a film thickness of the light emitting layer is preferably 5 to 50 nm, more preferably 7 to 50 nm and most preferably 10 to 50 nm. If it is less than 5 nm, it is difficult to form the light emitting layer, and controlling of the chromaticity is likely to become difficult. On the other hand, if it exceeds 50 nm, the operating voltage is likely to go up.

(5) Hole Injecting and Transporting Layer (Hole Transporting Zone)

The hole injecting and transporting layer is a layer for assisting injection of a hole into the light emitting layer to transport it to the light emitting region, and it has a large hole mobility and shows usually as small ionization energy as 5.5 eV or less. A material which transports a hole to the light emitting layer by a lower electric field strength is preferred for the above hole injecting and transporting layer, and more preferred is a material in which a mobility of a hole is at least $10^{-4}$ cm$^2$/V·second in applying an electric field of, for example, $10^4$ to $10^6$ V/cm.

When the aromatic amine derivative of the present invention is used in the hole transporting zone, the hole injecting and transporting layers may be formed from the aromatic amine derivative of the present invention alone or it may be used in a mixture with other materials.

The materials for forming the hole injecting and transporting layer by mixing with the aromatic amine derivative of the present invention shall not specifically be restricted as long as they have the preferred properties described above, and capable of being used are optional materials selected from materials which have so far conventionally been used as charge transporting materials for holes in photoconductive materials and publicly known materials which are used for a hole injecting and transporting layer in an organic EL device. In the present invention, a material which has a hole transporting ability and which can be used for a hole transporting zone is called a hole transporting material.

The specific examples thereof include triazole derivatives (refer to U.S. Pat. No. 3,112,197 and the like), oxadiazole derivatives (refer to U.S. Pat. No. 3,189,447 and the like), imidazole derivatives (refer to Japanese Patent Publication No. 16096/1962 and the like), polyarylalkane derivatives (refer to U.S. Pat. No. 3,615,402, ditto U.S. Pat. No. 3,820,989 and ditto U.S. Pat. No. 3,542,544, Japanese Patent Publication No. 555/1970 and ditto No. 10983/1976 and Japanese Patent Application Laid-Open No. 93224/1976, ditto No. 17105/1980, ditto No. 4148/1981, ditto No. 108667/1980, ditto No. 156953/1980 and ditto No. 36656/1981 and the like), pyrazoline derivatives and pyrazolone derivatives (refer to U.S. Pat. No. 3,180,729 and ditto U.S. Pat. No. 4,278,746 and Japanese Patent Application Laid-Open No. 88064/1980, ditto No. 88065/1980, ditto No. 105537/1974, ditto No. 51086/1980, ditto No. 80051/1981, ditto No. 88141/1981, ditto No. 45545/1982, ditto No. 112637/1979 and ditto No. 74546/1980 and the like), phenylenediamine derivatives (refer to U.S. Pat. No. 3,615,404, Japanese Patent Publication No. 10105/1976, ditto No. 3712/1971 and ditto No. 25336/1972 and Japanese Patent Application Laid-Open No. 119925/1979 and the like), arylamine derivatives (refer to U.S. Pat. No. 3,567,450, ditto U.S. Pat. No. 3,240,597, ditto U.S. Pat. No. 3,658,520, ditto U.S. Pat. No. 4,232,103, ditto U.S. Pat. No. 4,175,961 and ditto U.S. Pat. No. 4,012,376, Japanese Patent Publication No. 35702/1974 and ditto No. 27577/1964, Japanese Patent Application Laid-Open No. 144250/1980, ditto No. 119132/1981 and ditto No. 22437/1981 and German Patent No. 1,110,518 and the like), amino-substituted chalcone derivatives (refer to U.S. Pat. No. 3,526,501 and the like), oxazole derivatives (disclosed in U.S. Pat. No. 3,257,203 and the like), styrylanthracene derivatives (refer to Japanese Patent Application Laid-Open No. 46234/1981 and the like), fluorenone derivatives (refer to Japanese Patent Application Laid-Open No. 110837/1979 and the like), hydrazone derivatives (refer to U.S. Pat. No. 3,717,462, Japanese Patent Application Laid-Open No. 59143/1979, ditto No. 52063/1980, ditto No. 52064/1980, ditto No. 46760/1980, ditto No. 11350/1982 and ditto No. 148749/1982, Japanese Patent Application Laid-Open No. 311591/1990 and the like), stilbene derivatives (refer to Japanese Patent Application Laid-Open No. 210363/1986, ditto No. 228451/1986, ditto No. 14642/1986, ditto No. 72255/1986, ditto No. 47646/1987, ditto No. 36674/1987, ditto No. 10652/1987, ditto No. 30255/1987, ditto No. 93455/1985, ditto No. 94462/1985, ditto No. 174749/1985 and ditto No. 175052/1985 and the like), silazane derivatives (U.S. Pat. No. 4,950,950), polysilane base (Japanese Patent Application Laid-Open No. 204996/1990) and aniline base copolymers (Japanese Patent Application Laid-Open No. 282263/1990).

The compounds described above can be used as the material for the hole injecting and transporting layer, and preferably used are porphyrin compounds (disclosed in Japanese Patent Application Laid-Open No. 295695/1988 and the like), aromatic tertiary amine compounds and styrylamine compounds (refer to U.S. Pat. No. 4,127,412 and Japanese Patent Application Laid-Open No. 27033/1978, ditto No. 58445/1979, ditto No. 79450/1980, ditto No. 144250/1980, ditto No. 119132/1981, ditto No. 295558/1986, ditto No. 98353/1986 and ditto No. 295695/1988 and the like), and the aromatic tertiary amine compounds are particularly preferably used.

Further, capable of being given are compounds having two fused aromatic rings in a molecule described in U.S. Pat. No. 5,061,569, for example, 4,4'-bis(N-(1-naphthyl)-N-phenylamino)biphenyl (hereinafter abbreviated as NPD) and 4,4',4"-tris(N-(3-methylphenyl)-N-phenylamino)triphenylamine (hereinafter abbreviated as MTDATA) in which three triphenylamine units are combined in the form of a star burst type disclosed in Japanese Patent Application Laid-Open No. 308688/1992.

In addition to the above compounds, a nitrogen-containing heterocyclic derivative represented by the following formula which is disclosed in Japanese Patent No. 3571977 can be used as well:

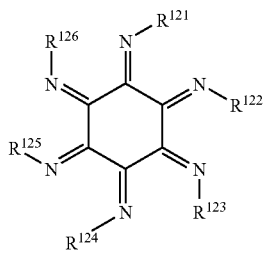

(wherein $R^{112}$ to $R^{126}$ each represent any of a substituted or non-substituted alkyl group, a substituted or non-substituted aryl group, a substituted or non-substituted aralkyl group and a substituted or non-substituted heterocyclic group; provided that $R^{121}$ to $R^{126}$ may be the same or different; $R^{121}$ and $R^{122}$, $R^{123}$ and $R^{124}$, $R^{125}$ and $R^{126}$, $R^{121}$ and $R^{126}$, $R^{122}$ and $R^{123}$ and $R^{124}$ and $R^{125}$ may form fused rings).

Further, a compound represented by the following formula which is described in U.S. Patent Application Publication 2004/0113547 can be used as well:

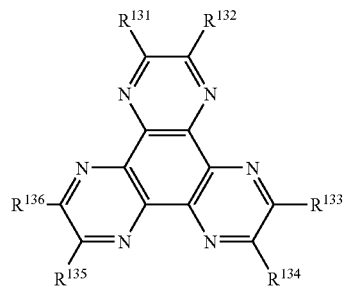

(wherein $R^{131}$ to $R^{136}$ are substituents and are preferably electron attractive groups such as a cyano group, a nitro group, a sulfonyl group, a carbonyl group, a trifluoromethyl group, halogen and the like).

As represented by the above materials, acceptor materials can also be used as the hole injecting material. The specific examples thereof have been described above.

Further, inorganic compounds such as p type Si, p type SiC and the like can also be used as the material for the hole injecting and transporting layer in addition to the aromatic dimethylidene base compounds described above shown as the material for the light emitting layer.

The hole injecting and transporting layer can be formed by making a thin film from the aromatic amine derivative of the present invention by a publicly known method such as, for example, a vacuum vapor deposition method, a spin coating method, a casting method, an LB method and the like. A film thickness of the hole injecting and transporting layer shall not specifically be restricted, and it is usually 5 nm to 5 μm. The above hole injecting and transporting layer may be constituted from a single layer comprising at least one of the materials described above as long as the aromatic amine derivative of the present invention is contained in the hole transporting zone, and a hole injecting and transporting layer comprising a compound which is different from the compound used in the hole injecting and transporting layer described above may be laminated thereon.

Further, an organic semiconductor layer may be provided as a layer for assisting injection of a hole into the light emitting layer, and the layer having a conductance of $10^{-10}$ S/cm or more is suited. Capable of being used as a material for the above organic semiconductor layer are conductive oligomers such as thiophene-containing oligomers and arylamine-containing oligomers disclosed in Japanese Patent Application Laid-Open No. 193191/1996 and conductive dendrimers such as arylamine-containing dendrimers.

(6) Electron Injecting and Transporting Layer

The electron injecting and transporting layer is a layer assisting injection of an electron into the light emitting layer to transport it to the light emitting region, and it has a large electron mobility. Also, the adhesion improving layer is a layer comprising particularly a material having a good adhesive property with the cathode in the above electron injecting layer.

It is known that since light emitted in an organic EL device is reflected by an electrode (in this case, a cathode), light emitted directly from an anode is interfered with light emitted via reflection by the electrode. In order to make efficient use of the above interference effect, the electron transporting layer is suitably selected in a film thickness of several nm to several μm, and particularly when the film thickness is large, the electron mobility is preferably at least $10^{-5}$ cm$^2$/Vs or more in applying an electric field of $10^4$ to $10^6$ V in order to avoid a rise in voltage.

The materials used for the electron injecting layer are suitably metal complexes of 8-hyroxyquinoline or derivatives thereof and oxadiazole derivatives. The specific examples of the metal complexes of 8-hyroxyquinoline or the derivatives thereof described above include metal chelate oxynoid compounds containing chelates of oxine (in general, 8-quinolinol or 8-hyroxyquinoline), and, for example, tris(8-quinolinol) aluminum can be used as the electron injecting material.

On the other hand, the oxadiazole derivative includes electron transmitting compounds represented by the following formulas:

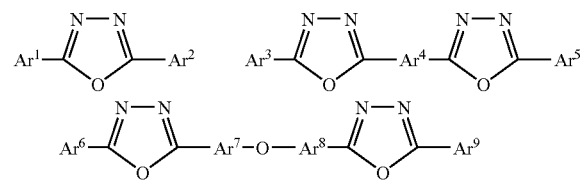

(wherein Ar$^1$, Ar$^2$, Ar$^3$, Ar$^5$, Ar$^6$ and Ar$^9$ each represent a substituted or non-substituted aryl group, and they may be the same as or different from each other; Ar$^4$, Ar$^7$ and Ar$^8$ each represent a substituted or non-substituted arylene group, and they may be the same as or different from each other).

In this connection, the aryl group includes phenyl, biphenylyl, anthryl, perylenyl and pyrenyl. Also, the arylene group includes phenylene, naphthylene, biphenylene, anthrylene, perylenylene, pyrenylene and the like. The substituents therefor include an alkyl group having 1 to 10 carbon atoms, an alkoxy group having 1 to 10 carbon atoms, a cyano group and the like. The above electron transmitting compounds have preferably a thin film-forming property.

The following compounds can be given as the specific examples of the electron transmitting compounds described above:

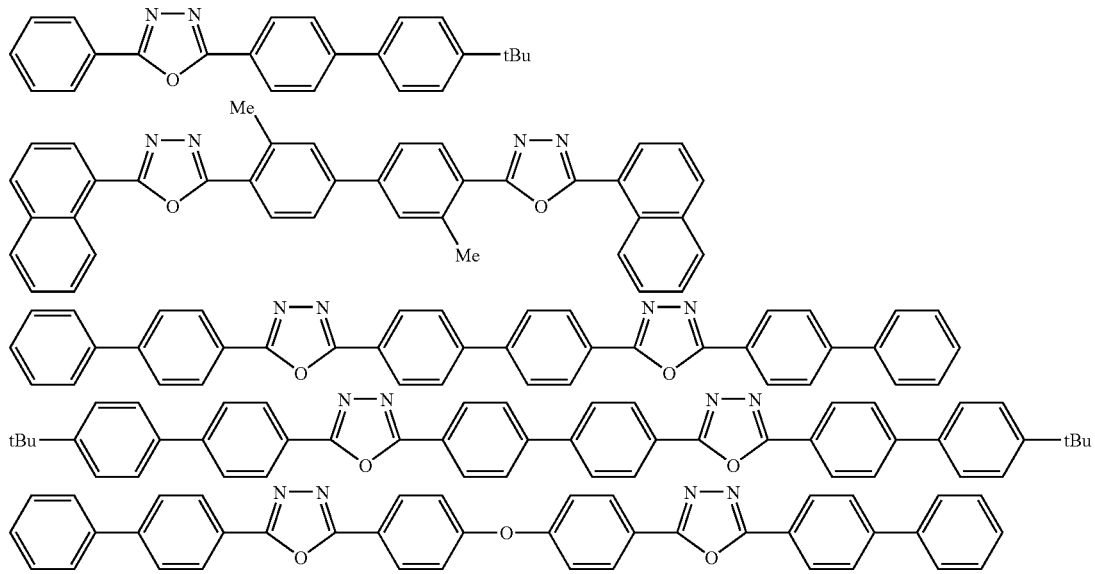

Further, Compounds represented by the following Formulas (A) to (F) can also be used as the materials used for the electron injecting layer and the electron transporting layer.

Nitrogen-containing heterocyclic derivative represented by:

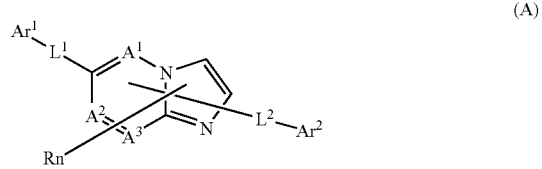

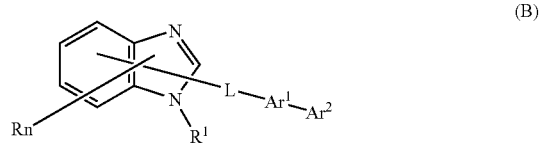

(in Formulas (A) and (B), A$^1$ to A$^3$ each are independently a nitrogen atom or a carbon atom;

in Formula (A), Ar$^1$ is a substituted or non-substituted aryl group having 6 to 60 ring carbon atoms or a substituted or non-substituted heteroaryl group having 3 to 60 ring carbon atoms; in Formula (B), Ar$_1$ is a divalent arylene group into which Ar$^1$ in Formula (A) is converted; Ar$^2$ is a hydrogen atom, a substituted or non-substituted aryl group having 6 to 60 ring carbon atoms, a substituted or non-substituted heteroaryl group having 3 to 60 ring carbon atoms, a substituted or non-substituted alkyl group having 1 to 20 carbon atoms or a substituted or non-substituted alkoxy group having 1 to 20 carbon atoms or a divalent group thereof; provided that any one of Ar$^1$ and Ar$^2$ is a substituted or non-substituted fused ring group having 10 to 60 ring carbon atoms or a substituted or non-substituted monohetero fused ring group having 3 to 60 ring carbon atoms or a divalent group thereof;

$L_1$, $L_2$ and L each are independently a single bond, a substituted or non-substituted arylene group having 6 to 60 ring carbon atoms, a substituted or non-substituted heteroarylene group having 3 to 60 ring carbon atoms or a substituted or non-substituted fluorenylene group;

R is a hydrogen atom, a substituted or non-substituted aryl group having 6 to 60 ring carbon atoms, a substituted or non-substituted heteroaryl group having 3 to 60 ring carbon atoms, a substituted or non-substituted alkyl group having 1 to 20 carbon atoms or a substituted or non-substituted alkoxy group having 1 to 20 carbon atoms; n is an integer of 0 to 5; when n is 2 or more, plural R's may be the same or different, and adjacent plural R's may be combined with each other to form a carbocyclic aliphatic ring or a carbocyclic aromatic ring;

$R^1$ is a hydrogen atom, a substituted or non-substituted aryl group having 6 to 60 ring carbon atoms, a substituted or non-substituted heteroaryl group having 3 to 60 ring carbon atoms, a substituted or non-substituted alkyl group having 1 to 20 carbon atoms, a substituted or non-substituted alkoxy group having 1 to 20 carbon atoms or -L-$Ar_1$—$Ar^2$).

Nitrogen-containing heterocyclic derivative represented by:

(wherein HAr is a nitrogen-containing heterocycle having 3 to 40 carbon atoms which may have a substituent; L is a single bond, an arylene group having 6 to 60 carbon atoms which may have a substituent, a heteroarylene group having 3 to 60 carbon atoms which may have a substituent or a fluorenylene group which may have a substituent; $Ar_1$ is a divalent aromatic hydrocarbon group having 6 to 60 carbon atoms which may have a substituent; and $Ar^2$ is an aryl group having 6 to 60 carbon atoms which may have a substituent or a heteroaryl group having 3 to 60 carbon atoms which may have a substituent).

Silacyclopentadiene derivative represented by:

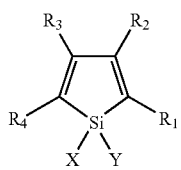

(wherein X and Y each are independently a saturated or unsaturated hydrocarbon group having 1 to 6 carbon atoms, an alkoxy group, an alkenyloxy group, an alkynyloxy group, a hydroxy group, a substituted or non-substituted aryl group, a substituted or non-substituted heterocycle or a structure in which X is combined with Y to form a saturated or unsaturated ring; $R^1$ to $R^4$ each are independently a hydrogen atom, a halogen atom, a substituted or non-substituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, a cyano group or a structure in which when two substituents are adjacent, they are bonded with each other to form a substituted or non-substituted, saturated or unsaturated ring).

Borane derivative represented by:

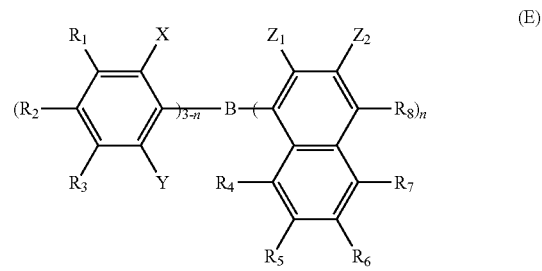

(wherein $R_1$ to $R_8$ and $Z_2$ each represent independently a hydrogen atom, a saturated or unsaturated hydrocarbon group, an aromatic group, a heterocyclic group, a substituted amino group, a substituted boryl group, an alkoxy group or an aryloxy group; X, Y and $Z_1$ each represent independently a saturated or unsaturated hydrocarbon group, an aromatic group, a heterocyclic group, a substituted amino group, an alkoxy group or an aryloxy group; substituents of $Z_1$ and $Z_2$ may be combined with each other to form a fused ring; n represents an integer of 1 to 3, and when n is 2 or more, $Z_1$'s may be different; provided that a case in which n is 1 and X, Y and $R_2$ are methyl and in which $R_8$ is a hydrogen atom or a substituted boryl group and a case in which n is 3 and $Z_1$ is methyl are not included therein).

[wherein $Q^1$ and $Q^2$ each represent independently a ligand represented by the following Formula (G), and L represents a halogen atom, a substituted or non-substituted alkyl group, a substituted or non-substituted cycloalkyl group, a substituted or non-substituted aryl group, a substituted or non-substituted heterocyclic group, —$OR^1$ ($R^1$ is a hydrogen atom, a substituted or non-substituted alkyl group, a substituted or non-substituted cycloalkyl group, a substituted or non-substituted aryl group or a substituted or non-substituted heterocyclic group) or a ligand represented by —O—Ga-$Q^3$ ($Q^4$) ($Q^3$ and $Q^4$ are the same as $Q^1$ and $Q^2$)]:

[wherein rings $A^1$ and $A^2$ assume a six-membered aryl ring structure which may have a substituent and in which they are fused with each other].

The above metal complex has a strong property of an n type semiconductor and is provided with a large electron injecting ability. Further, since it has low production energy in forming the complex, a bonding property between the metal and the ligand in the metal complex formed becomes firm, and a fluorescence quantum efficiency of the light emitting material grows larger as well.

The specific examples of substituents for the rings $A^1$ and A2 forming the ligand represented by Formula (G) include a halogen atom such as chlorine, bromine, iodine and fluorine, a substituted or non-substituted alkyl group such as methyl, ethyl, propyl, butyl, s-butyl, t-butyl, pentyl, hexyl, heptyl, octyl, stearyl, trichloromethyl and the like, a substituted or non-substituted aryl group such as phenyl, naphthyl, 3-methylphenyl, 3-methoxyphenyl, 3-fluorophenyl, 3-trichloromethylphenyl, 3-trifluoromethylphenyl, 3-nitrophenyl and the like, a substituted or non-substituted alkoxy group such as methoxy, n-butoxy, t-butoxy, trichloromethoxy, trifluoroethoxy, pentafluoropropoxy, 2,2,3,3-tetrafluoropropoxy, 1,1,1, 3,3,3-hexafluoro-2-propoxy, 6-(perfluoroethyl)hexyloxy and the like, a substituted or non-substituted aryloxy group such as phenoxy, p-nitrophenoxy, p-t-butylphenoxy, 3-fluorophenoxy, pentafluorophenoxy, 3-trifluoromethylphenoxy and the like, a substituted or non-substituted alkylthio group such as methylthio, ethylthio, t-butylthio, hexylthio, octylthio, trifluoromethylthio and the like, a substituted or non-substituted arylthio group such as phenylthio, p-nitrophenylthio, p-t-butylphenylthio, 3-fluorophenylthio, pentafluorophenylthio, 3-trifluoromethylphenylthio and the like, a cyano group, a nitro group, an amino group, a mono- or disubstituted amino group such as methylamino, diethylamino, ethylamino, diethylamino, dipropylamino, dibutylamino, diphenylamino and the like, an acylamino group such as bis(acetoxymethyl) amino, bis(acetoxyethyl)amino, bis(acetoxypropyl)amino, bis(acetoxybutyl)amino and the like, a hydroxyl group, a siloxy group, an acyl group, a carbamoyl group such as methylcarbamoyl, dimethylcarbamoyl, ethylcarbamoyl, diethylcarbamoyl, propylcarbamoyl, butylcarbamoyl, phenylcarbamoyl and the like, a carboxylic acid group, a sulfonic acid group, an imide group, a cycloalkyl group such as cyclopentane, cyclohexyl and the like, an aryl group such as phenyl, naphthyl, biphenylyl, anthryl, phenanthryl, fluorenyl, pyrenyl and the like and a heterocyclic group such as pyridinyl, pyrazinyl, pyrimidinyl, pyridazinyl, triazinyl, indolinyl, quinolinyl, acridinyl, pyrrolidinyl, dioxanyl, piperidinyl, morpholidinyl, piperazinyl, carbazolyl, furanyl, thiophenyl, oxazolyl, oxadiazolyl, benzoxazolyl, thiazolyl, thiadiazolyl, benzothiazolyl, triazolyl, imidazolyl, benzimidazolyl, furanyl and the like. Further, the substituents described above may be combined with each other to form six-membered aryl rings or heterocycles.

The preferred mode of the organic EL device of the present invention includes a device containing a reducing dopant in the region which transports an electron or an interfacial region between the cathode and the organic layer. In this case, the reducing dopant is defined by a substance which can reduce an electron transporting compound. Accordingly, various compounds can be used as long as they have a certain reducing property, and capable of being suitably used is at least one substance selected from the group consisting of, for example, alkali metals, alkaline earth metals, rare earth metals, oxides of alkali metals, halides of alkali metals, oxides of alkaline earth metals, halides of alkaline earth metals, oxides of rare earth metals or halides of rare earth metals, organic complexes of alkali metals, organic complexes of alkaline earth metals and organic complexes of rare earth metals.

To be more specific, the preferred reducing dopant includes at least one alkali metal selected from the group consisting of Li (work function: 2.9 eV), Na (work function: 2.36 eV), K (work function: 2.28 eV), Rb (work function: 2.16 eV) and Cs (work function: 1.95 eV) and at least one alkali earth metal selected from the group consisting of Ca (work function: 2.9 eV), Sr (work function: 2.0 to 2.5 eV) and Ba (work function: 2.52 eV), and the compounds having a work function of 2.9 eV or less are particularly preferred. Among them, the more preferred reducing dopant is at least one alkali metal selected from the group consisting of K, Rb and Cs, and it is more preferably Rb or Cs. It is most preferably Cs. The above alkali metals have a particularly high reducing ability, and addition of a relatively small amount thereof to the electron injecting zone makes it possible to raise a light emitting luminance in the organic EL device and extend a lifetime thereof. The combination of two or more kinds of the above alkali metals is preferred as the reducing dopant having a work function of 2.9 eV or less, and particularly preferred is the combination containing Cs, for example, the combination of Cs with Na, Cs with K, Cs with Rb or Cs with Na and K. Containing Cs in combination makes it possible to efficiently exhibit the reducing ability, and addition thereof to the electron injecting zone makes it possible to enhance a light emitting luminance in the organic EL device and extend a lifetime thereof.

In the present invention, an electron injecting layer constituted from an insulator and a semiconductor may further be provided between the cathode and the organic layer. In this case, an electric current can effectively be prevented from leaking to enhance the electron injecting property. Preferably used as the above insulator is at least one metal compound selected from the group consisting of alkali metal chalcogenides, alkaline earth metal chalcogenides, halides of alkali metals and halides of alkaline earth metals. If the electron injecting layer is constituted from the above alkali metal chalcogenides and the like, it is preferred from the viewpoint that the electron injecting property can further be enhanced. To be specific, the preferred alkali metal chalcogenides include, for example, $Li_2O$, $K_2O$, $Na_2S$, $Na_2Se$ and $Na_2O$, and the preferred alkaline earth metal chalcogenides include, for example, CaO, BaO, SrO, BeO, BaS and CaSe. Also, the preferred halides of alkali metals include, for example, LiF, NaF, KF, LiCl, KCl and NaCl. Further, the preferred halides of alkaline earth metals include, for example, fluorides such as $CaF_2$, $BaF_2$, $SrF_2$, $MgF_2$ and $BeF_2$ and halides other than the fluorides.

The semiconductor constituting the electron transporting layer includes a single kind of oxides, nitrides or nitride oxides containing at least one element of Ba, Ca, Sr, Yb, Al, Ga, In, Li, Na, Cd, Mg, Si, Ta, Sb and Zn or combinations of two or more kinds thereof. The inorganic compound constituting the electron transporting layer is preferably a crystallite or amorphous insulating thin film. If the electron transporting layer is constituted from the above insulating thin film, the more homogeneous thin film is formed, and therefore picture element defects such as dark spots can be reduced. The above inorganic compound includes the alkali metal chalcogenides, the alkaline earth metal chalcogenides, the halides of alkali metals and the halides of alkaline earth metals each described above.

(7) Cathode

Cathodes prepared by using metals, alloys, electroconductive compounds and mixtures thereof each having a small work function (4 eV or less) for electrode materials are used as the cathode in order to inject electrons into the electron injecting and transporting layer or the light emitting layer. The specific examples of the above electrode materials include sodium, sodium-potassium alloys, magnesium, lithium, magnesium-silver alloys, aluminum/aluminum oxide, aluminum-lithium alloys, indium, rare earth metals and the like.

The above cathode can be prepared by forming a thin film from the above electrode materials by a method such as vapor deposition, sputtering and the like.

In this respect, when light emitted from the light emitting layer is taken out from the cathode, a light transmittance of the cathode based on light emitted is preferably larger than 10%.

A sheet resistance of the cathode is preferably several hundred $\Omega/\square$ or less, and a film thickness thereof is usually 10 nm to 1 µm, preferably 50 to 200 nm.

(8) Insulating Layer

The organic EL device is liable to cause picture element defects by leak and short since an electric field is applied to a ultrathin film. In order to prevent the above matter, an insulating thin film layer is preferably interposed between a pair of the electrodes.

A material used for the insulating layer includes, for example, aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide and the like, and mixtures and laminates thereof may be used as well.

(9) Production Process for Organic EL Device

According to the materials and the forming methods which have been shown above as the examples, the anode, the light emitting layer, if necessary, the hole injecting and transporting layer and, if necessary, the electron injecting and transporting layer are formed, and further the cathode is formed, whereby the organic EL device can be prepared. Also, the organic EL device can be prepared as well in an order of from the cathode to the anode which is reverse to the order described above.

A preparation example of an organic EL device having a structure in which an anode/a hole injecting layer/a light emitting layer/an electron injecting layer/a cathode are provided in order on a light transmitting substrate shall be described below.

First, a thin film comprising an anode material is formed on a suitable light transmitting substrate by a method such as vapor deposition, sputtering and the like so that a film thickness falling in a range of 1 µm or less, preferably 10 to 200 nm is obtained, whereby an anode is prepared. Next, a hole injecting layer is provided on the above anode. The hole injecting layer can be formed, as described above, by a method such as a vacuum vapor deposition method, a spin coating method, a casting method, an LB method and the like, and it is formed preferably by the vacuum vapor deposition method from the viewpoints that the homogeneous film is liable to be obtained and that pinholes are less liable to be produced. When forming the hole injecting layer by the vacuum vapor deposition method, the depositing conditions thereof are varied according to the compounds used (materials for the hole injecting layer), the crystal structure of the targeted hole injecting layer and the recombination structure, and in general, they are suitably selected preferably in the ranges of a depositing source temperature of 50 to 450° C., a vacuum degree of $10^{-7}$ to $10^{-3}$ Torr, a depositing speed of 0.01 to 50 nm/second, a substrate temperature of −50 to 300° C. and a film thickness of 5 nm to 5 µm.

Next, a light emitting layer can be formed on the hole injecting layer by making a thin film from the desired organic light emitting material by a method such as a vacuum vapor deposition method, sputtering, a spin coating method, a casting method and the like, and it is formed preferably by the vacuum vapor deposition method from the viewpoints that the homogeneous film is liable to be obtained and that pinholes are less liable to be produced. When forming the light emitting layer by the vacuum vapor deposition method, the depositing conditions thereof are varied according to the compounds used, and in general, they can be selected from the same condition ranges as in the hole injecting layer.

Next, an electron injecting layer is provided on the above light emitting layer. It is formed preferably by the vacuum vapor deposition method as in the case with the hole injecting layer and the light emitting layer since the homogeneous film has to be obtained. The depositing conditions thereof can be selected from the same condition ranges as in the hole injecting layer and the light emitting layer.

The aromatic amine derivative of the present invention can be codeposited together with the other materials, though varied depending on that it is added to any layer of the light emitting zone and the hole transporting zone, when using the vacuum vapor deposition method. When using the spin coating method, it can be added by mixing with the other materials.

Lastly, a cathode is laminated, whereby an organic EL device can be obtained.

The cathode is constituted from metal, and therefore the vapor deposition method and the sputtering method can be used. However, the vacuum vapor deposition method is preferred in order to protect the organic substance layer of the base from being damaged in making the film.

The above organic EL device is preferably prepared serially from the anode up to the cathode after vacuuming once.

The forming methods of the respective layers in the organic EL device of the present invention shall not specifically be restricted, and forming methods carried out by a vacuum vapor deposition method, a spin coating method and the like which have so far publicly been known can be used. The organic thin film layer containing the compound represented by Formula (1) described above which is used for the organic EL device of the present invention can be formed by a publicly known method carried out by a vacuum vapor deposition method, a molecular beam epitaxy method (MBE method) and a coating method such as a dipping method using a solution prepared by dissolving the compound in a solvent, a spin coating method, a casting method, a bar coating method and a roll coating method.

The film thicknesses of the respective organic layers in the organic EL device of the present invention shall not specifically be restricted, and in general, if the film thicknesses are too small, defects such as pinholes are liable to be caused. On the other hand, if they are too large, high voltage has to be applied, and the efficiency is deteriorated, so that they fall preferably in a range of several nm to 1 µm.

When applying a direct voltage to the organic EL device, light emission can be observed by applying a voltage of 5 to 40 V setting a polarity of the anode to plus and that of the cathode to minus. An electric current does not flow by applying a voltage at a reverse polarity, and light emission is not caused at all. Further, when applying an AC voltage, uniform light emission can be observed only when the anode has a plus polarity and the cathode has a minus polarity. A waveform of an alternating current applied may be optional.

EXAMPLES

The present invention shall be explained in further details below with reference to synthetic examples and examples. Intermediates 1 to 17 produced in Synthetic Examples 1 to 17 have the following structures:

Intermediate 1 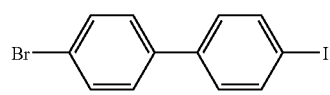 Intermediate 2 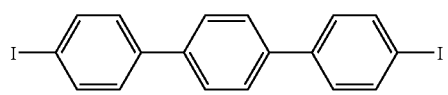
Intermediate 3 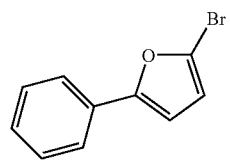 Intermediate 4 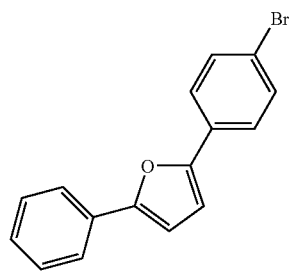
Intermediate 5 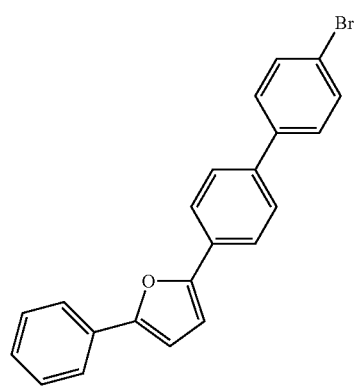 Intermediate 6 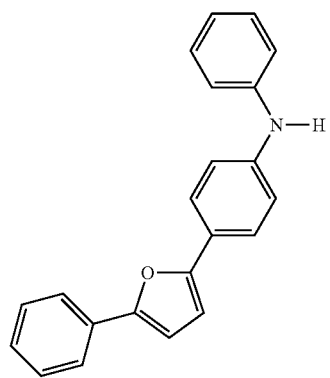
Intermediate 7 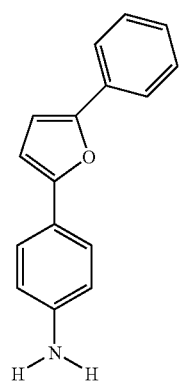 Intermediate 8 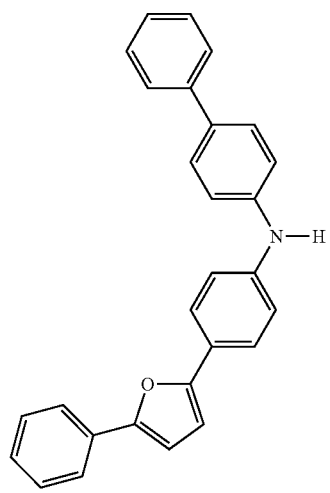

-continued
Intermediate 9
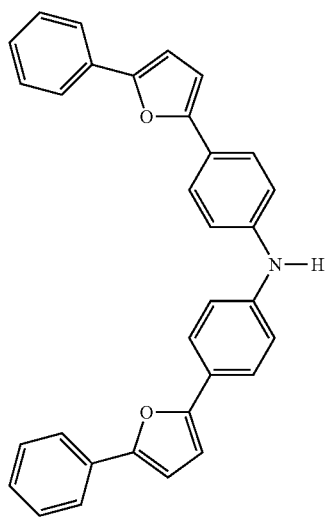
Intermediate 10
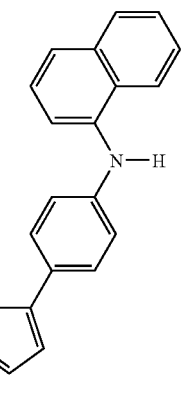
Intermediate 11
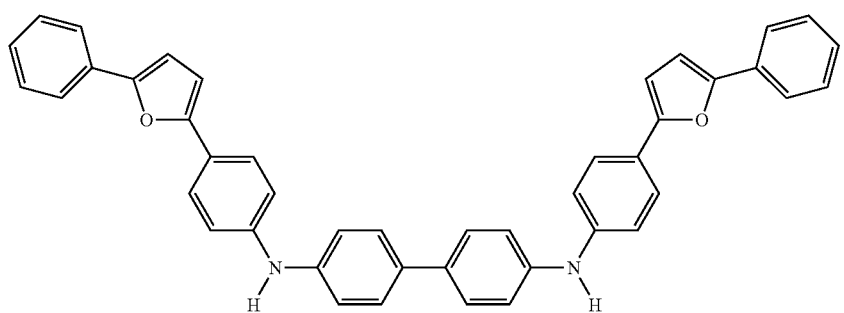
Intermediate 12
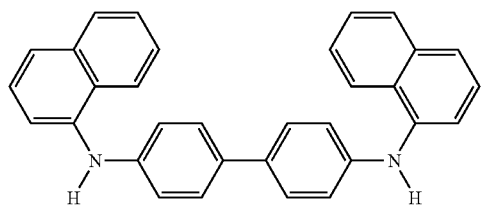
Intermediate 13
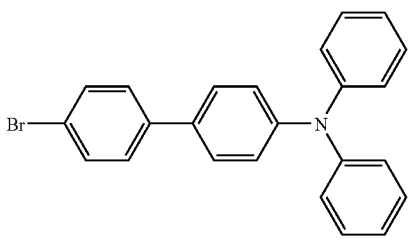
Intermediate 14
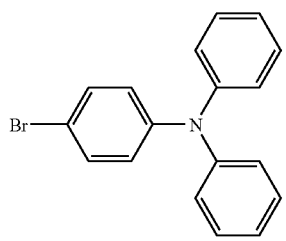
Intermediate 15
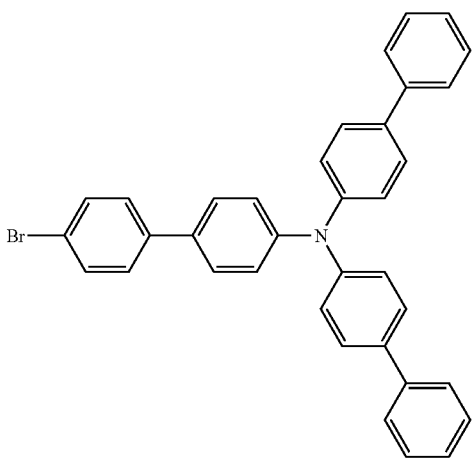

Synthetic Example 1

Synthesis of Intermediate 1

A three neck flask of 1000 ml was charged with 47 g of 4-bromobiphenyl, 23 g of iodine, 9.4 g of periodic acid dihydrate, 42 ml of water, 360 mL of acetic acid and 11 mL of sulfuric acid under argon flow, and the mixture was stirred at 65° C. for 30 minutes and then reacted at 90° C. for 6 hours. The reaction product was poured into ice and water and filtered. The filtered matter was washed with water and then with methanol, whereby 67 g of a white powder was obtained. The principal peak of m/z=358 and 360 versus $C_{12}H_{15}BrI=359$ was obtained by analysis of FD-MS (field desorption mass spectrum), and therefore it was identified as Intermediate 1.

Synthetic Example 2

Synthesis of Intermediate 2

A three neck flask of 300 ml was charged with 10 g of p-terphenyl, 12 g of iodine, 4.9 g of periodic acid dihydrate, 20 mL of water, 170 mL of acetic acid and 22 mL of sulfuric acid under argon flow, and the mixture was stirred at 65° C. for 30 minutes and then reacted at 90° C. for 6 hours. The reaction product was poured into ice and water and filtered. The filtered matter was washed with water and then with methanol, whereby 18 g of a white powder was obtained. The principal peak of m/z=482 versus $C_{18}H_{12}I_2=482$ was obtained by analysis of FD-MS (field desorption mass spectrum), and therefore it was identified as Intermediate 2.

Synthetic Example 3

Synthesis of Intermediate 3

A reaction vessel of 50 L was charged with 750 g of phenylboronic acid, 900 g of 2-bromothiophene, 142 g of tetrakis(triphenylphosphine)palladium (Pd(PPh$_3$)$_4$), 9 L of a sodium carbonate (Na$_2$CO$_3$) solution of 2M and 15 L of dimethoxyethane under argon flow, and then they were reacted at 80° C. for 8 hours. The reaction solution was extracted with toluene/water, and the extract was dried on anhydrous sodium sulfate. This was concentrated under reduced pressure, and a crude product obtained was refined through a column, whereby 708 g of a white powder was obtained.

A reaction vessel of 20 L was charged with 708 g of the compound obtained above and 8 L of N,N-dimethylforamide (DMF) under argon flow, and then 960 g of N-bromosuccinimide (NBS) was slowly added thereto to carry out reaction at room temperature for 12 hours. The reaction solution was extracted with hexane/water, and the extract was dried on anhydrous sodium sulfate. This was concentrated under reduced pressure, and a crude product obtained was refined through a column, whereby 632 g of a white powder was obtained. It was identified as Intermediate 3 by analysis of FD-MS (field desorption mass spectrum).

Synthetic Example 4

Synthesis of Intermediate 4

A reaction vessel of 20 L was charged with 632 g of Intermediate 3 and 7 L of anhydrous tetrahydrofuran (THF) under argon flow and cooled down to −30° C. n-Butyhl-lithium (n-BuLi, 1.6M hexane solution) 2.3 L was added thereto to carry out reaction for one hour. After cooled down to −70° C., 1658 g of triisopropyl borate (manufactured by Tokyo Kasei Kogyo Co., Ltd.) was added thereto. The solution was slowly heated and stirred at room temperature for one hour. After adding 1.7 L of 10% hydrochloric acid solution, the mixture was stirred. The reaction solution was extracted with ethyl acetate and water, and the organic layer was washed with water. The organic layer was dried on anhydrous sodium sulfate, and the solvent was removed by distillation. The residue was washed with hexane, whereby 330 g of a white powder was obtained.

A reaction vessel of 20 L was charged with 466 g of 5-phenyl-2-thiopheneboronic acid obtained above, 600 g of 4-iodobromobenzene, 41 g of tetrakis(triphenylphosphine)-palladium (Pd(PPh$_3$)$_4$), 2.6 L of 2M solution of sodium carbonate (Na$_2$CO$_3$) and 10 L of dimethoxyethane under argon flow, and then they were reacted at 80° C. for 8 hours. The reaction solution was extracted with toluene/water, and the extract was dried on anhydrous sodium sulfate. This was concentrated under reduced pressure, and a crude product obtained was refined through a column, whereby 263 g of a white powder was obtained. It was identified as Intermediate 4 by analysis of FD-MS (field desorption mass spectrum).

Synthetic Example 5

Synthesis of Intermediate 5

Reaction was carried out in the same manner, except that in synthesis of Intermediate 4, Intermediate 1 was used in place of 4-iodobromobenzene, whereby 274 g of a white powder was obtained. It was identified as Intermediate 5 by analysis of FD-MS (field desorption mass spectrum).

Synthetic Example 6

Synthesis of Intermediate 6

A flask was charged with 5.5 g of aniline, 14.9 g of Intermediate 4, 6.8 g of sodium t-butoxide (manufactured by Hiroshima Wako Co., Ltd.), 0.46 g of tris(dibenzylideneacetone)dipalladium(0) (manufactured by Aldrich Co., Ltd.) and 300 mL of anhydrous toluene under argon flow to carry out reaction at 80° C. for 8 hours.

After cooling down, 500 ml of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 8.6 g of a pale yellow powder was obtained. It was identified as Intermediate 6 by analysis of FD-MS (field desorption mass spectrum).

Synthetic Example 7

Synthesis of Intermediate 7

A flask was charged with 185 g of acetamide Intermediate 4, 300 g of Intermediate 4 (manufactured by Wako Pure Chemical Industries, Ltd.), 544 g of potassium carbonate (manufactured by Wako Pure Chemical Industries, Ltd.), 12.5 g of copper powder (manufactured by Wako Pure Chemical Industries, Ltd.) and 2 L of decalin under argon flow to carry out reaction at 190° C. for 4 days. The reaction solution was cooled down after finishing the reaction, and 2 L of toluene was added to obtain insoluble matters by filtration. The filtered matter was dissolved in 4.5 L of chloroform to remove insoluble matters, and then the solution was subjected to treatment with activated carbon and concentrated. Acetone 3 L was added thereto to obtain 165 g of deposited crystal by filtration.

This was suspended in 5 L of ethylene glycol (manufactured by Wako Pure Chemical Industries, Ltd.) and 50 mL of water, and 210 g of a 85% potassium hydroxide aqueous solution was added thereto, followed by carrying out reaction at 120° C. for 8 hours. After finishing the reaction, the reaction liquid was poured into 10 L of water, and deposited crystal was obtained by filtration and washed with water and methanol. The crystal thus obtained was dissolved in 3 L of tetrahydrofuran by heating. The solution was treated with activated carbon and then concentrated, and acetone was added thereto to deposit crystal. This was separated by filtration to obtain 127 g of a white powder. It was identified as Intermediate 7 by analysis of FD-MS (field desorption mass spectrum).

Synthetic Example 8

Synthesis of Intermediate 8

A flask was charged with 185 g of acetamide (manufactured by Tokyo Kasei Kogyo Co., Ltd.), 253 g of 4-bromobiphenyl (manufactured by Wako Pure Chemical Industries, Ltd.), 544 g of potassium carbonate (manufactured by Wako Pure Chemical Industries, Ltd.), 12.5 g of copper powder (manufactured by Wako Pure Chemical Industries, Ltd.) and 2 L of decalin under argon flow to carry out reaction at 190° C. for 4 days. The reaction solution was cooled down after finishing the reaction, and 2 L of toluene was added to obtain insoluble matters by filtration. The filtered matter was dissolved in 4.5 L of chloroform to remove insoluble matters, and then the solution was subjected to treatment with activated carbon and concentrated. Acetone 3 L was added thereto to obtain 205 g of deposited crystal by filtration.

Added thereto were 168 g of Intermediate 4, 380 g of potassium carbonate (manufactured by Wako Pure Chemical Industries, Ltd.), 8.8 g of copper powder (manufactured by Wako Pure Chemical Industries, Ltd.) and 2 L of decalin, and they were reacted at 190° C. for 4 days. The reaction solution was cooled down after finishing the reaction, and 1.4 L of toluene was added to obtain insoluble matters by filtration. The filtered matter was dissolved in 3 L of chloroform to remove insoluble matters, and then the solution was subjected to treatment with activated carbon and concentrated. Acetone 3 L was added thereto to obtain 224 g of deposited crystal by filtration. This was suspended in 3.5 L of ethylene glycol (manufactured by Wako Pure Chemical Industries, Ltd.) and 35 mL of water, and 147 g of a 85% potassium hydroxide aqueous solution was added thereto, followed by carrying out reaction at 120° C. for 8 hours. After finishing the reaction, the reaction liquid was poured into 10 L of water, and deposited crystal was obtained by filtration and washed with water and methanol. The crystal thus obtained was dissolved in 3 L of tetrahydrofuran by heating. The solution was treated with activated carbon and then concentrated, and acetone was added thereto to deposit crystal. This was separated by filtration to obtain 121 g of a white powder. It was identified as Intermediate 8 by analysis of FD-MS (field desorption mass spectrum).

Synthetic Example 9

Synthesis of Intermediate 9

Reaction was carried out in the same manner, except that in synthesis of Intermediate 7, an amount of Intermediate 4 was changed from 300 g to 600 g, whereby 212 g of a white powder was obtained. It was identified as Intermediate 9 by analysis of FD-MS (field desorption mass spectrum).

Synthetic Example 10

Synthesis of Intermediate 10

Reaction was carried out in the same manner, except that in synthesis of Intermediate 8,1-bromonaphthalene was used in place of 4-bromobiphenyl, whereby 9.2 g of a white powder was obtained. It was identified as Intermediate 10 by analysis of FD-MS (field desorption mass spectrum).

Synthetic Example 11

Synthesis of Intermediate 11

A flask was charged with 185 g of acetamide Intermediate 4, 300 g of Intermediate 4 (manufactured by Wako Pure Chemical Industries, Ltd.), 544 g of potassium carbonate (manufactured by Wako Pure Chemical Industries, Ltd.), 12.5 g of copper powder (manufactured by Wako Pure Chemical Industries, Ltd.) and 2 L of decalin under argon flow to carry out reaction at 190° C. for 4 days. The reaction solution was cooled down after finishing the reaction, and 2 L of toluene was added to obtain insoluble matters by filtration. The filtered matter was dissolved in 4.5 L of chloroform to remove insoluble matters, and then the solution was subjected to treatment with activated carbon and concentrated. Acetone 3 L was added thereto to obtain 165 g of deposited crystal by filtration.

Added thereto were 120 g of 4,4'-diiodobiphenyl (manufactured by Wako Pure Chemical Industries, Ltd.), 163 g of potassium carbonate (manufactured by Wako Pure Chemical Industries, Ltd.), 3.8 g of copper powder (manufactured by Wako Pure Chemical Industries, Ltd.) and 600 mL of decalin, and they were reacted at 190° C. for 4 days.

The reaction solution was cooled down after finishing the reaction, and 600 mL of toluene was added thereto to obtain insoluble matters by filtration. The filtered matter was dissolved in 1.4 L of chloroform to remove insoluble matters, and then the solution was subjected to treatment with activated carbon and concentrated. Acetone 1 L was added thereto to obtain 361 g of deposited crystal by filtration.

This was suspended in 1.5 L of ethylene glycol (manufactured by Wako Pure Chemical Industries, Ltd.) and 15 mL of water, and 44 g of a 85% potassium hydroxide aqueous solution was added thereto, followed by carrying out reaction at 120° C. for 8 hours. After finishing the reaction, the reaction liquid was poured into 10 L of water, and deposited crystal was obtained by filtration and washed with water and methanol. The crystal thus obtained was dissolved in 1 L of tetrahydrofuran by heating. The solution was treated with activated carbon and then concentrated, and acetone was added thereto to deposit crystal. This was separated by filtration to obtain 107 g of a white powder. It was identified as Intermediate 11 by analysis of FD-MS (field desorption mass spectrum).

Synthetic Example 12

Synthesis of Intermediate 12

A flask was charged with 547 g of 1-acetamidenaphthalene (manufactured by Tokyo Kasei Kogyo Co., Ltd.), 400 g of 4,4'-diiodobiphenyl (manufactured by Wako Pure Chemical Industries, Ltd.), 544 g of potassium carbonate (manufactured by Wako Pure Chemical Industries, Ltd.), 12.5 g of copper powder (manufactured by Wako Pure Chemical Industries, Ltd.) and 2 L of decalin under argon flow to carry out reaction at 190° C. for 4 days.

The reaction solution was cooled down after finishing the reaction, and 2 L of toluene was added thereto to obtain insoluble matters by filtration. The filtered matter was dissolved in 4.5 L of chloroform to remove insoluble matters, and then it was subjected to treatment with activated carbon and concentrated. Acetone 3 L was added thereto to obtain 382 g of deposited crystal by filtration. This was suspended in 5 L of ethylene glycol (manufactured by Wako Pure Chemical Industries, Ltd.) and 50 mL of water, and 145 g of a 85% potassium hydroxide aqueous solution was added thereto, followed by carrying out reaction at 120° C. for 8 hours. After finishing the reaction, the reaction liquid was poured into 10 L of water, and deposited crystal was obtained by filtration and washed with water and methanol. The crystal thus obtained was dissolved in 3 L of tetrahydrofuran by heating. The solution was treated with activated carbon and then concentrated, and acetone was added thereto to deposit crystal. This was separated by filtration to obtain 264 g of a white powder. It was identified as Intermediate 12 by analysis of FD-MS (field desorption mass spectrum).

Synthetic Example 13

Synthesis of Intermediate 13

A flask was charged with 5.1 g of diphenylamine, 10.8 g of Intermediate 1, 3 g of sodium t-butoxide (manufactured by Hiroshima Wako Co., Ltd.), 0.5 g of bis(triphenylphosphine)palladium(II) chloride (manufactured by Tokyo Kasei Kogyo Co., Ltd.) and 500 mL of xylene under argon flow to carry out reaction at 130° C. for 24 hours.

After cooling down, 1000 ml of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 3.4 g of a pale yellow powder was obtained. It was identified as Intermediate 13 by analysis of FD-MS (field desorption mass spectrum).

Synthetic Example 14

Synthesis of Intermediate 14

Reaction was carried out in the same manner, except that in synthesis of Intermediate 13, 4-iodobromobenzene was used in place of Intermediate 1, whereby 2.8 g of a white powder was obtained. It was identified as Intermediate 14 by analysis of FD-MS (field desorption mass spectrum).

Synthetic Example 15

Synthesis of Intermediate 15

A three neck flask of 200 ml was charged with 20.0 g of 4-bromobiphenyl (manufactured by Tokyo Kasei Kogyo Co., Ltd.), 8.64 g of sodium t-butoxide (manufactured by Wako Pure Chemical Industries, Ltd.) and 84 mg of palladium acetate (manufactured by Wako Pure Chemical Industries, Ltd.). Further, a stirring rod was put therein, and rubber caps were set at both sided necks of the flask. A condenser for refluxing was set in the neck of the center, and a three-way cock and a balloon charged with argon gas were set thereon to substitute the inside of the system three times with the argon gas in the balloon by means of a vacuum pump.

Next, 120 mL of dehydrated toluene (manufactured by Hiroshima Wako Co., Ltd.), 4.08 mL of benzylamine (manufactured by Tokyo Kasei Kogyo Co., Ltd.) and 338 μL of tris-t-butylphosphine (a 2.22 mol/L toluene solution, manufactured by Aldrich Co., Ltd.) were added thereto through a rubber septum by means of a syringe and stirred at room temperature for 5 minutes. Next, the flask was set on an oil bath and gradually heated up to 120° C. while stirring the solution. After 7 hours passed, the flask was taken off from the oil bath to terminate the reaction, and it was left standing for 12 hours under argon atmosphere. The reaction solution was transferred into a separating funnel, and 600 mL of dichloromethane was added thereto to dissolve the precipitate. The solution was washed with 120 mL of a saturated brine, and then the organic layer was dried on anhydrous potassium carbonate. The solvent of the organic layer obtained by removing potassium carbonate by filtration was removed by distillation, and 400 mL of toluene and 80 mL of ethanol were added to the resulting residue. The flask to which a drying tube was mounted was heated to 80° C. to completely dissolve the residue. Then, the flask was left standing for 12 hours and slowly cooled down to room temperature to thereby expedite recrystallization. Deposited crystal was separated by filtration and dried under vacuum at 60° C., whereby 13.5 g of N,N-di-(4-biphenylyl)-benzylamine was obtained. A single neck flask of 300 mL was charged with 1.35 g of N,N-di-(4-biphenylyl)-benzylamine and 135 mg of palladium-activated carbon (palladium content: 10% by weight, manufactured by Hiroshima Wako Co., Ltd.), and 100 mL of chloroform and 20 mL of ethanol were added to dissolve it. Next, a stirring rod was put in the flask, and then a three-way cock which was equipped with a balloon filled with 2 L of hydrogen gas was mounted to the flask. The inside of the flask was substituted 10 times with hydrogen gas by means of a vacuum pump. Lost hydrogen gas was newly filled to set a volume of hydrogen gas again to 2 L, and then the solution was vigorously stirred at room temperature. After stirring for 30 hours, 100 mL of dichloromethane was added thereto, and the catalyst was separated by filtration. Next, the solution obtained was transferred into a separating funnel and washed with 50 mL of a sodium hydrogencarbonate saturated aqueous solution, and then the organic layer was separated and dried on anhydrous potassium carbonate. After filtered, the solvent was removed by distillation, and 50 mL of toluene was added to the resulting residue to carry out recrystallization. Deposited crystal was separated by filtration and dried under vacuum at 50° C., whereby 0.99 g of di-4-biphenylylamine was obtained.

A flask was charged with 10 g of di-4-biphenylylamine, 9.7 g of 4,4'-dibromobiphenyl (manufactured by Tokyo Kasei Kogyo Co., Ltd.), 3 g of sodium t-butoxide (manufactured by Hiroshima Wako Co., Ltd.), 0.5 g of bis(triphenylphosphine)-palladium(II) chloride (manufactured by Tokyo Kasei Kogyo Co., Ltd.) and 500 ml of xylene under argon flow to carry out reaction at 130° C. for 24 hours. After cooling down, 1000 ml of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 9.1 g of 4'-bromo-N,N-dibiphenylyl-4-amino-1,1'-biphenyl (Intermediate 15) was obtained.
Shown below are the structures of compounds H1 to H16 which are the aromatic amine derivatives of the present invention produced in Synthetic Practical Examples 1 to 15:
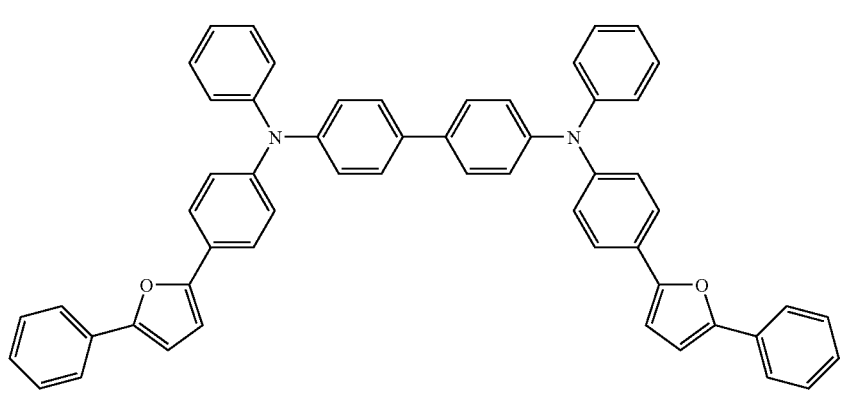

H4
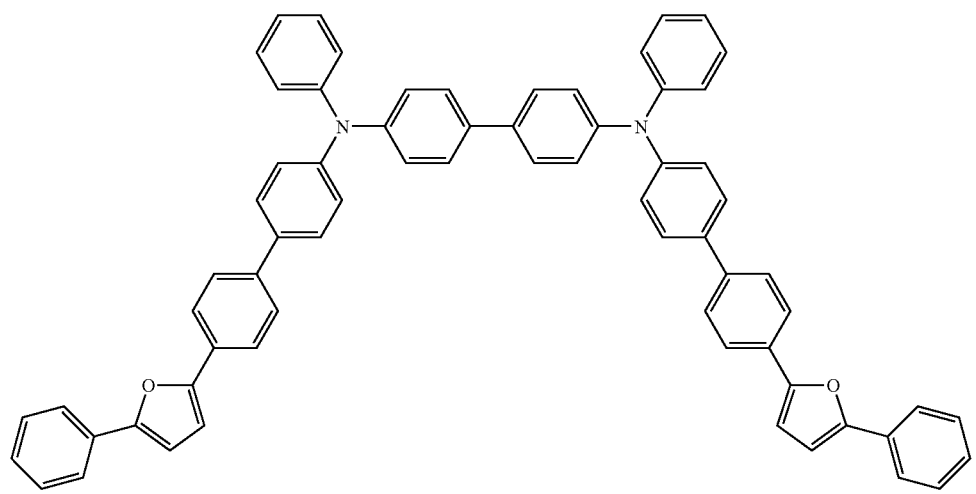
H5
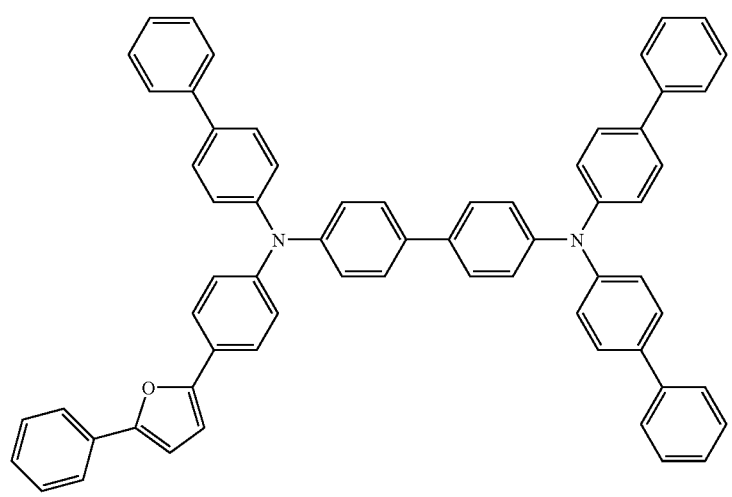
H6
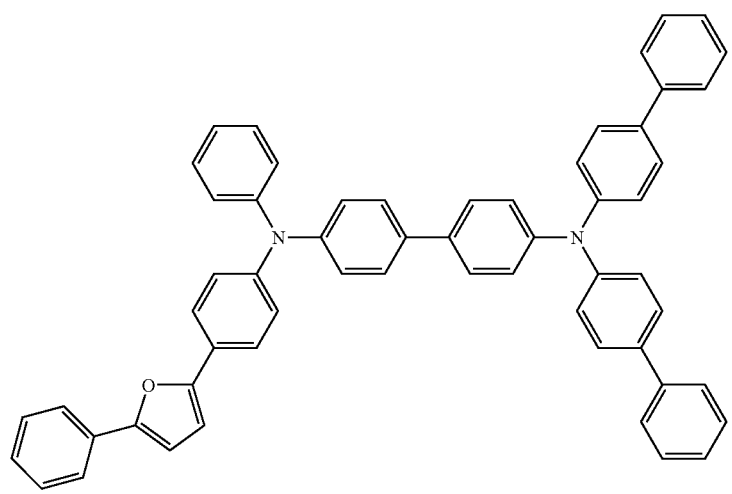

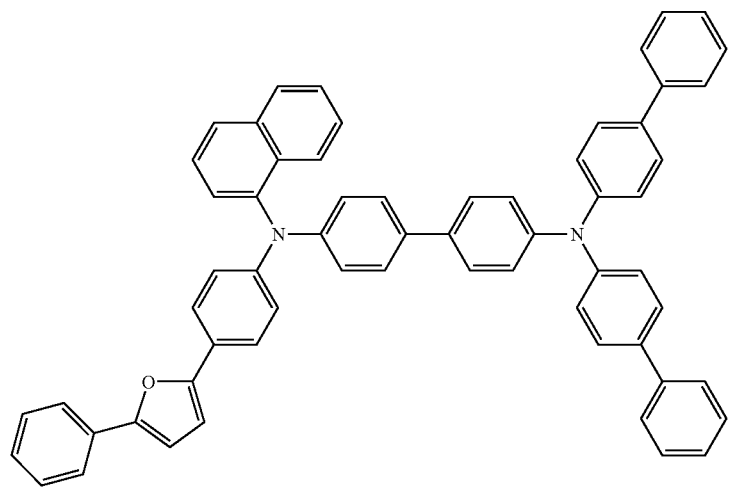
H7
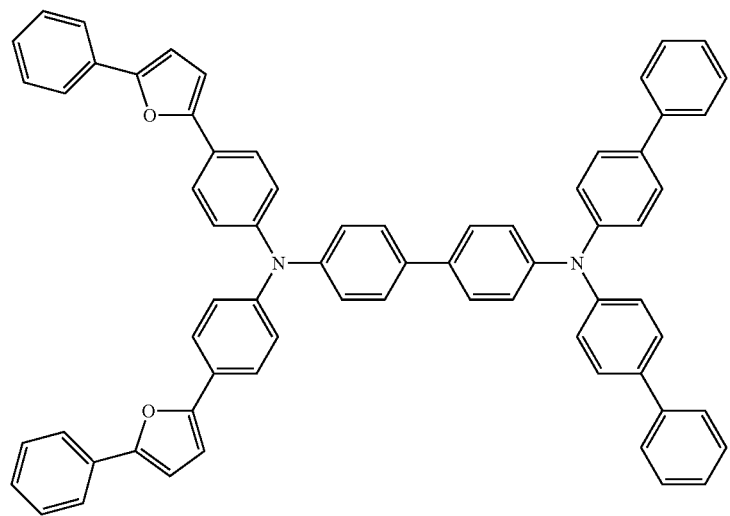
H8
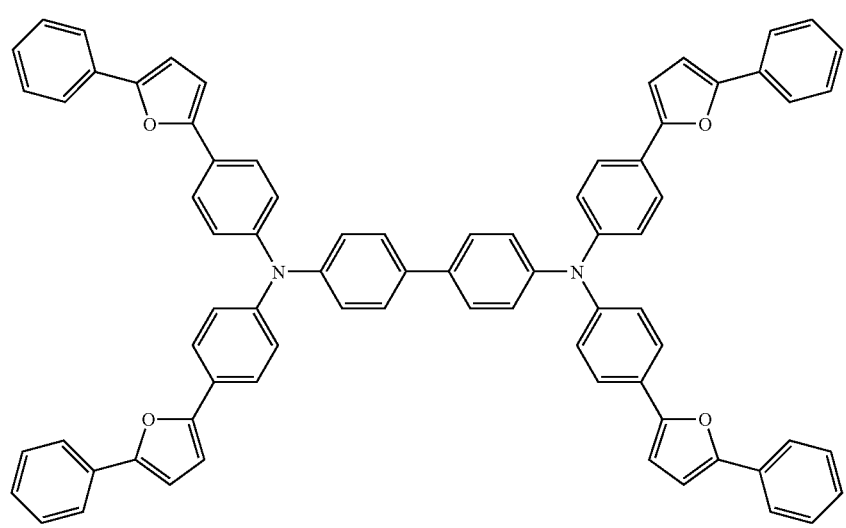
H9

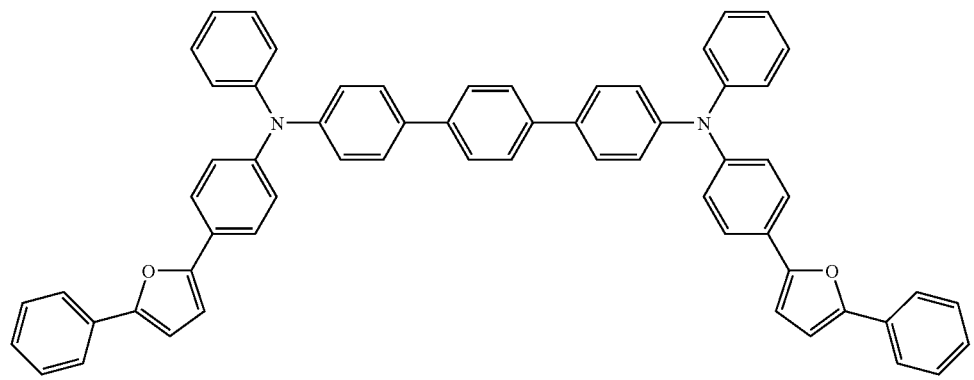
H10
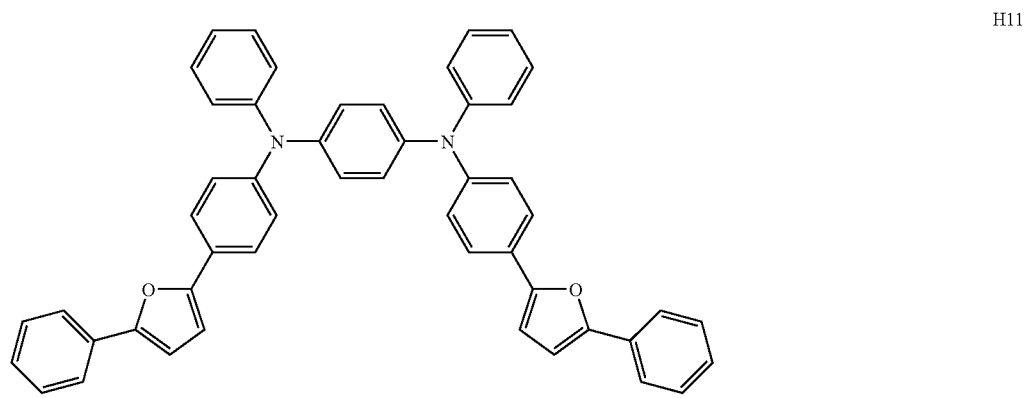
H11
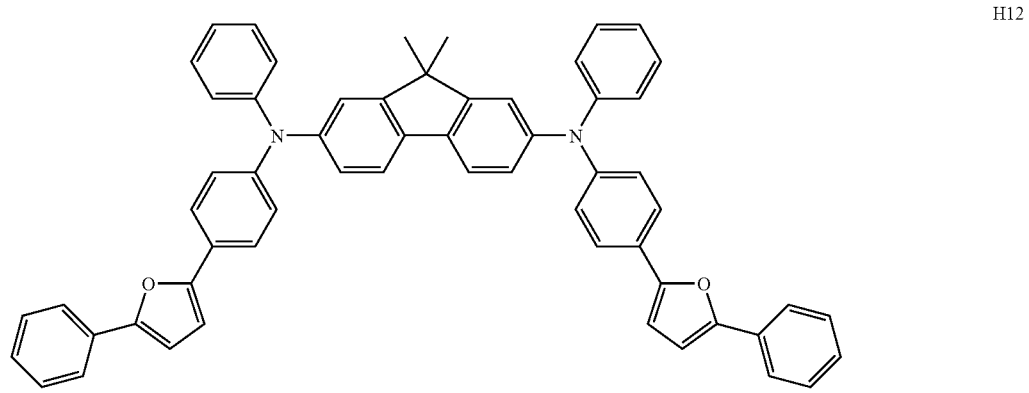
H12

-continued
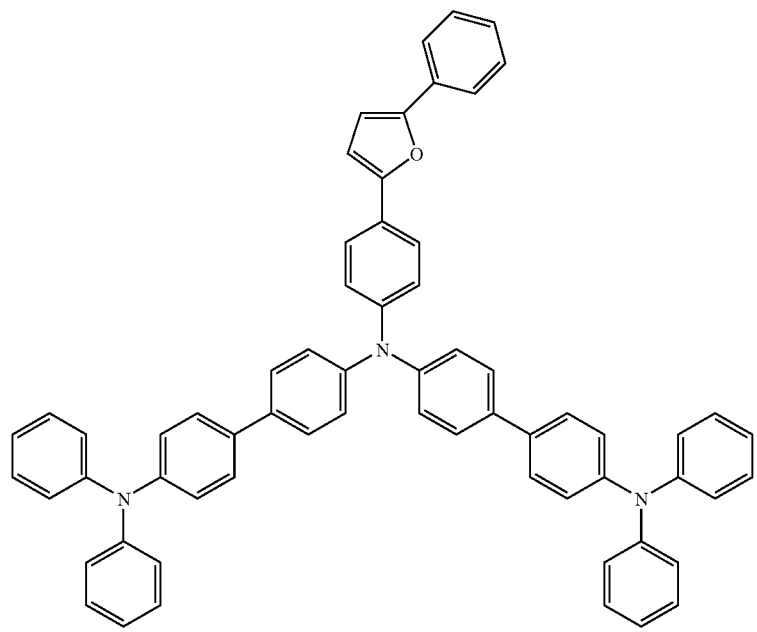
H13
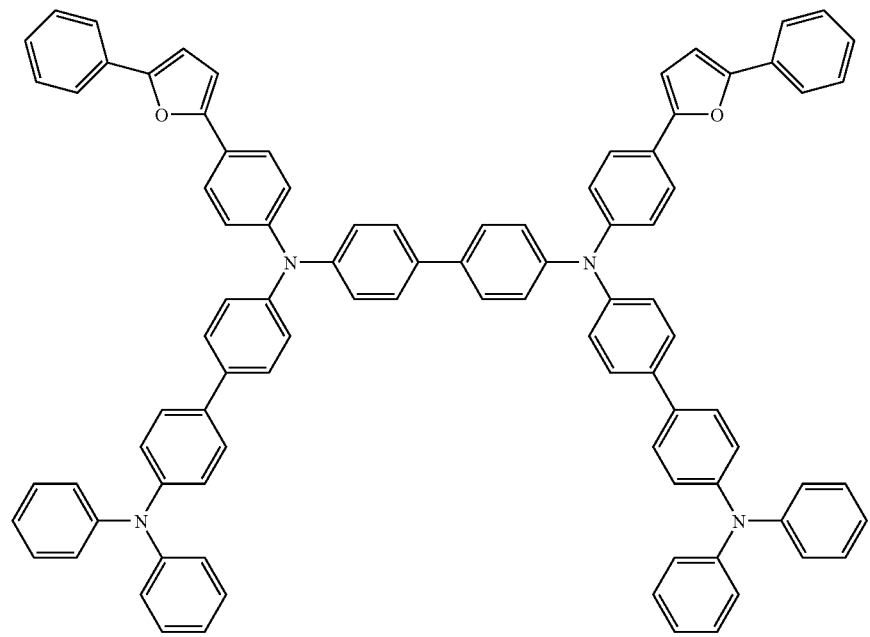
H14

H15

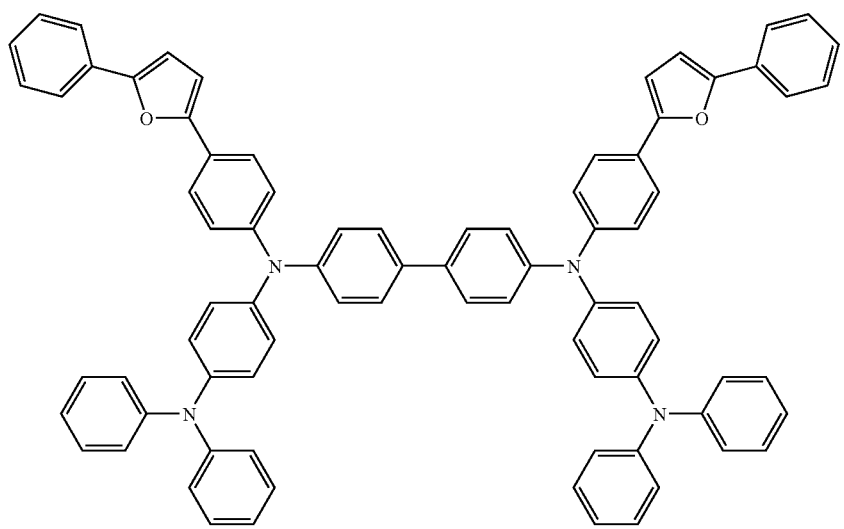

H16

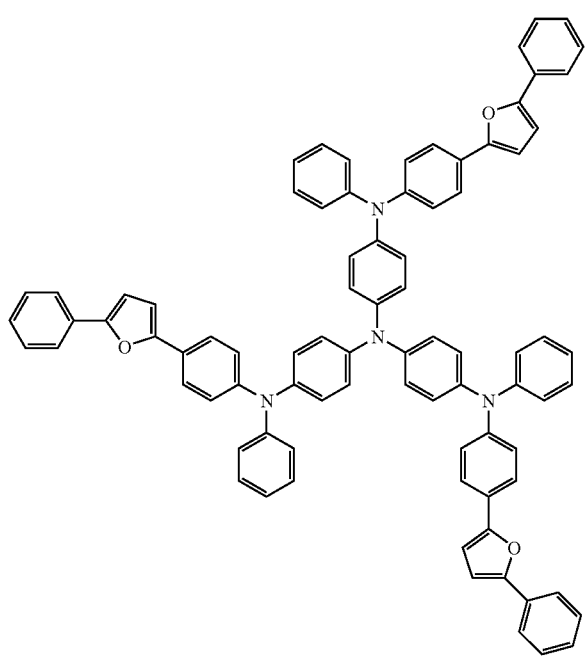

Synthetic Practical Example 1

Synthesis of Compound H1

A flask was charged with 3.4 g of N,N'-diphenylbenzidine, 6.3 g of Intermediate 4, 2.6 g of sodium t-butoxide (manufactured by Hiroshima Wako Co., Ltd.), 92 mg of tris(dibenzylideneacetone)dipalladium(O) (manufactured by Aldrich Co., Ltd.), 42 mg of tri-t-butylphosphine and 100 mL of anhydrous toluene under argon flow to carry out reaction at 80° C. for 8 hours.

After cooling down, 500 mL of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 3.2 g of a pale yellow powder was obtained. It was identified as the compound H1 by analysis of FD-MS (field desorption mass spectrum).

Synthetic Practical Example 2

Synthesis of Compound H2

A flask was charged with 4.1 g of 4,4'-diiodobiphenyl, 8.1 g of Intermediate 8, 2.6 g of sodium t-butoxide (manufactured by Hiroshima Wako Co., Ltd.), 92 mg of tris(dibenzylideneacetone)dipalladium(0) (manufactured by Aldrich Co., Ltd.), 42 mg of tri-t-butylphosphine and 100 mL of anhydrous toluene under argon flow to carry out reaction at 80° C. for 8 hours.

After cooling down, 500 mL of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 3.9 g of a pale yellow powder was obtained. It was identified as the compound H2 by analysis of FD-MS (field desorption mass spectrum).

Synthetic Practical Example 3

Synthesis of Compound H3

Reaction was carried out in the same manner, except that in Synthetic Practical Example 1, 4.4 g of Intermediate 12 was used in place of N,N'-diphenylbenzidine, whereby 5.1 g of a pale yellow powder was obtained. It was identified as the compound H3 by analysis of FD-MS (field desorption mass spectrum).

Synthetic Practical Example 4

Synthesis of Compound H4

Reaction was carried out in the same manner, except that in Synthetic Practical Example 1, 7.8 g of Intermediate 5 was used in place of Intermediate 4, whereby 4.7 g of a pale yellow powder was obtained. It was identified as the compound H4 by analysis of FD-MS (field desorption mass spectrum).

Synthetic Practical Example 5

Synthesis of Compound H5

A flask was charged with 7.7 g of Intermediate 8, 11.0 g of Intermediate 15, 2.6 g of sodium t-butoxide (manufactured by Hiroshima Wako Co., Ltd.), 92 mg of tris(dibenzylideneacetone)dipalladium(0) (manufactured by Aldrich Co., Ltd.), 42 mg of tri-t-butylphosphine and 100 mL of anhydrous toluene under argon flow to carry out reaction at 80° C. for 8 hours.

After cooling down, 500 mL of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 9.1 g of a pale yellow powder was obtained. It was identified as the compound H5 by analysis of FD-MS (field desorption mass spectrum).

Synthetic Practical Example 6

Synthesis of Compound H6

Reaction was carried out in the same manner, except that in Synthetic Practical Example 5, 6.2 g of Intermediate 6 was used in place of Intermediate 8, whereby 6.1 g of a pale yellow powder was obtained. It was identified as the compound H6 by analysis of FD-MS (field desorption mass spectrum).

Synthetic Practical Example 7

Synthesis of Compound H7

Reaction was carried out in the same manner, except that in Synthetic Practical Example 5, 7.2 g of Intermediate 10 was used in place of Intermediate 8, whereby 5.5 g of a pale yellow powder was obtained. It was identified as the compound H7 by analysis of FD-MS (field desorption mass spectrum).

Synthetic Practical Example 8

Synthesis of Compound H8

Reaction was carried out in the same manner, except that in Synthetic Practical Example 5, 9.1 g of Intermediate 9 was used in place of Intermediate 8, whereby 7.2 g of a pale yellow powder was obtained. It was identified as the compound H8 by analysis of FD-MS (field desorption mass spectrum).

Synthetic Practical Example 9

Synthesis of Compound H9

Reaction was carried out in the same manner, except that in Synthetic Practical Example 2, 9.5 g of Intermediate 9 was used in place of Intermediate 8, whereby 4.1 g of a pale yellow powder was obtained. It was identified as the compound H9 by analysis of FD-MS (field desorption mass spectrum).

Synthetic Practical Example 10

Synthesis of Compound H10

Reaction was carried out in the same manner, except that in Synthetic Practical Example 2, 4.8 g of Intermediate 2 was used in place of 4,4'-diiodobiphenyl and that 6.5 g of Intermediate 6 was used in place of Intermediate 8, whereby 3.2 g of a pale yellow powder was obtained. It was identified as the compound H10 by analysis of FD-MS (field desorption mass spectrum).

Synthetic Practical Example 11

Synthesis of Compound H11

Reaction was carried out in the same manner, except that in Synthetic Practical Example 2, 3.3 g of 1,4-diiodobenzene was used in place of 4,4'-diiodobiphenyl and that 6.5 g of Intermediate 6 was used in place of Intermediate 8, whereby 2.5 g of a pale yellow powder was obtained. It was identified as the compound H11 by analysis of FD-MS (field desorption mass spectrum).

Synthetic Practical Example 12

Synthesis of Compound H12

Reaction was carried out in the same manner, except that in Synthetic Practical Example 2, 3.5 g of 2,7-dibromo-9,9-dimethylfluorene was used in place of 4,4'-diiodobiphenyl and that 6.5 g of Intermediate 6 was used in place of Intermediate 8, whereby 3.1 g of a pale yellow powder was obtained. It was identified as the compound H12 by analysis of FD-MS (field desorption mass spectrum).

Synthetic Practical Example 13

Synthesis of Compound H13

Reaction was carried out in the same manner, except that in Synthetic Practical Example 1, 2.3 g of Intermediate 7 was used in place of N,N'-diphenylbenzidine and that 8.0 g of Intermediate 13 was used in place of Intermediate 4, whereby 1.9 g of a pale yellow powder was obtained. It was identified as the compound H13 by analysis of FD-MS (field desorption mass spectrum).

Synthetic Practical Example 14

Synthesis of Compound H14

Reaction was carried out in the same manner, except that in Synthetic Practical Example 1, 6.2 g of Intermediate 11 was used in place of N,N'-diphenylbenzidine and that 8.0 g of Intermediate 13 was used in place of Intermediate 4, whereby 6.2 g of a pale yellow powder was obtained. It was identified as the compound H14 by analysis of FD-MS (field desorption mass spectrum).

Synthetic Practical Example 15

Synthesis of Compound H15

Reaction was carried out in the same manner, except that in Synthetic Practical Example 1, 6.5 g of Intermediate 11 was used in place of N,N'-diphenylbenzidine and that 6.5 g of Intermediate 14 was used in place of Intermediate 4, whereby 4.1 g of a pale yellow powder was obtained. It was identified as the compound H15 by analysis of FD-MS (field desorption mass spectrum).

Synthetic Practical Example 16

Synthesis of Compound H16

Reaction was carried out in the same manner, except that in Synthetic Practical Example 1, 9.3 g of Intermediate 6 was used in place of 4,4'-diiodobiphenyl and that 4.8 g of tris(4-bromophenyl)amine was used in place of Intermediate 12, whereby 4.1 g of a pale yellow powder was obtained. It was identified as the compound H16 by analysis of FD-MS (field desorption mass spectrum).

Example 1

Production of Organic EL Device

A glass substrate (manufactured by Geomatech Co., Ltd.) of 25 mm×75 mm×1.1 mm thickness equipped with a transparent electrode was subjected to supersonic wave washing in isopropyl alcohol for 5 minutes and then to UV ozone washing for 30 minutes.

After washed, the glass substrate equipped with an ITO transparent electrode line was loaded in a substrate holder of a vacuum vapor deposition apparatus, and a film of the compound H1 described above having a film thickness of 60 nm was formed on a face of a side at which the transparent electrode line was formed so that it covered the transparent electrode described above. This H1 film functions as a hole injecting layer. A film of a compound TBDB shown below having a film thickness of 20 nm was formed on the above Hi film. This film functions as a hole transporting layer. Further, a compound EM1 shown below was deposited thereon to form a film having a film thickness of 40 nm. At the same time, the following amine compound D1 having a styryl group was deposited as a light emitting molecule so that a weight ratio of EM1 to D1 was 40:2. This film functions as a light emitting layer.

A film of Alq shown below having a film thickness of 10 nm was formed on the above film. This film functions as an electron injecting layer. Then, Li (Li source: manufactured by Saesgetter Co., Ltd.) which was a reducing dopant and Alq were subjected to binary vapor deposition to form an Alq:Li film (film thickness: 10 nm) as an electron injecting layer (cathode). Metal Al was deposited on the above Alq:Li film to form a metal cathode, whereby an organic EL device was formed.

Further, a current efficiency of the organic EL device thus obtained was measured, and a light emitting color thereof was observed. The luminance was measured by means of CS1000 manufactured by Konica Minolta Co., Ltd. to calculate the current efficiency at 10 mA/cm$^2$. Further, the half lifetime thereof in light emission was measured at an initial luminance of 5000 cd/m$^2$ and room temperature in operating at a DC constant electric current, and the results thereof are shown in Table 1.

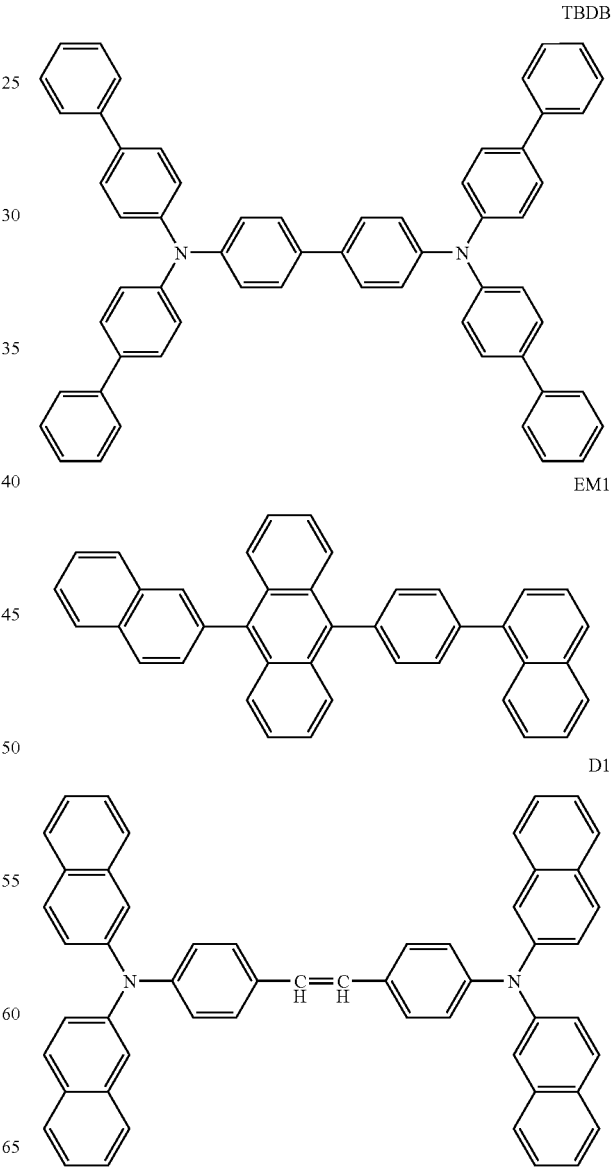

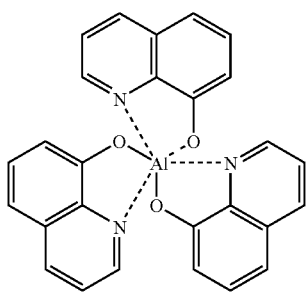

Alq

Examples 2 to 4

Production of Organic EL Devices

Organic EL devices were prepared in the same manner, except that in Example 1, compounds described in Table 1 were used as hole transporting materials in place of the compound H1.

The current efficiencies of the organic EL devices thus obtained were measured, and the light emitting colors thereof were observed. Further, the half lifetimes thereof in light emission were measured at an initial luminance of 5000 cd/m² and room temperature in operating at a DC constant electric current, and the results thereof are shown in Table 1.

Comparatives Example 1

An organic EL device was prepared in the same manner, except that in Example 1, a comparative compound 1 was used as a hole transporting material in place of the compound H1.

A current efficiency of the organic EL device thus obtained was measured, and a light emitting color thereof was observed. Further, the half lifetime thereof in light emission was measured at an initial luminance of 5000 cd/m² and room temperature in operating at a DC constant electric current, and the results thereof are shown in Table 1.

TABLE 1

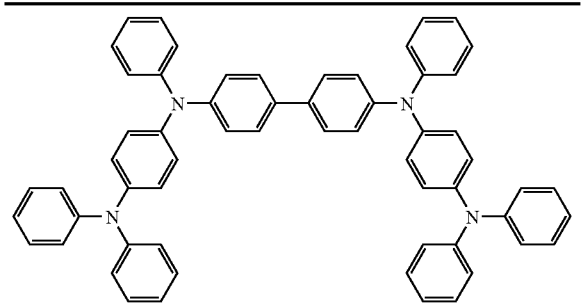

Comparative compound 1

| | Hole transporting material | Voltage (V) | Light emitting color | Half lifetime (hour) |
|---|---|---|---|---|
| Example 1 | H1 | 6.3 | blue | 330 |
| Example 2 | H3 | 6.2 | blue | 320 |
| Example 3 | H5 | 6.5 | blue | 350 |
| Example 4 | H6 | 6.4 | blue | 340 |
| Example 5 | H1 | 6.4 | blue | 370 |

TABLE 1-continued

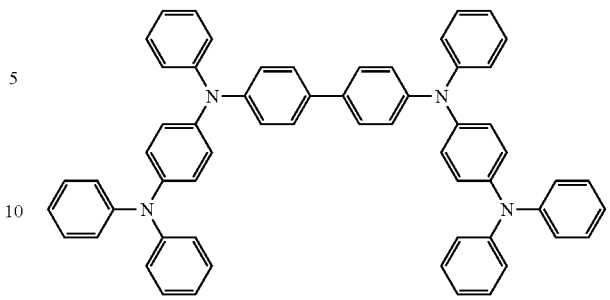

Comparative compound 1

| | Hole transporting material | Voltage (V) | Light emitting color | Half lifetime (hour) |
|---|---|---|---|---|
| Comparative Example 1 | Comparative compound 1 | 7.1 | blue | 280 |
| Comparative Example 2 | Comparative compound 1 | 7.0 | blue | 270 |

Example 5

Production of Organic EL Device

An organic EL device was prepared in the same manner, except that in Example 1, the following arylamine compound D2 was used in place of the amine compound D1 having a styryl group. Me is methyl.

A current efficiency of the organic EL device thus obtained was measured, and a light emitting color thereof was observed. Further, the half lifetime thereof in light emission was measured at an initial luminance of 5000 cd/m² and room temperature in operating at a DC constant electric current, and the results thereof are shown in Table 1.

D2

Comparatives Example 2

An organic EL device was prepared in the same manner, except that in Example 8, the comparative compound 1 described above was used as a hole transporting material in place of the compound H1.

A current efficiency of the organic EL device thus obtained was measured, and a light emitting color thereof was observed. Further, the half lifetime thereof in light emission

INDUSTRIAL APPLICABILITY

As explained above in details, the aromatic amine derivative of the present invention reduces the driving voltage and makes the molecules less liable to be crystallized, and addition thereof to the organic thin film layer makes it possible to enhance a yield in producing the organic EL device and materialize the organic EL device having a long lifetime.

What is claimed is:

1. An aromatic amine compound represented by the following Formula (1):

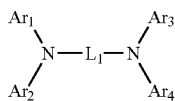

(1)

wherein $L_1$ represents a divalent group selected from the group consisting of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthaceyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, fluoranthenyl, fluorenyl, and 9,9-demethylfluorenyl;

at least one of $Ar_1$ to $Ar_4$ is represented by the following Formula (2):

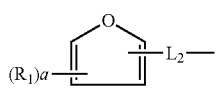

(2)

wherein $R_1$ an aryl group having 6 to 50 ring atoms, an alkyl group having 1 to 50 carbon atoms, a halogen atom or a cyano group;

a is an integer of 1 to 3; and $L_2$ represents a divalent group selected from the group consisting of phenyl, 1-naphthyl, 2-naphthyl, 2-biphenylyl, 3-biphenylyl, 4-biphenylyl, o-tolyl, m-tolyl, p-tolyl, fluoranthenyl, fluorenyl, and 9,9-dimethylfluorenyl;

in Formula (1), among $Ar_1$ to $Ar_4$, the groups which are not represented by Formula (2) each are independently an aryl group having 6 to 50 ring atoms; provided that substituents for $Ar_1$ to $Ar_4$ each are independently an aryl group having 6 to 50 ring atoms, a halogen atom or a cyano group.

2. The aromatic amine compound as described in claim 1, wherein in Formula (1) described above, $Ar_1$ is represented by Formula (2) described above.

3. The aromatic amine compound as described in claim 1, wherein in Formula (1) described above, $Ar_1$ and $Ar_2$ each are independently represented by Formula (2) described above.

4. The aromatic amine compound as described in claim 1, wherein in Formula (1) described above, $Ar_1$ and $Ar_3$ each are independently represented by Formula (2) described above.

5. The aromatic amine compound as described in claim 1, wherein in Formula (1) described above, three or more of $Ar_1$ to $Ar_4$ are different from each other and wherein the aromatic amine compound is asymmetric.

6. The aromatic amine compound as described in claim 1, wherein in Formula (1) described above, three of $Ar_1$ to $Ar_4$ are the same and wherein the aromatic amine compound is asymmetric.

7. The aromatic amine compound as described in claim 1, wherein in Formula (1) described above, $L_1$ is biphenylene, terphenylene or fluorenylene.

8. The aromatic amine compound as described in claim 1, wherein in Formula (2) described above, $L_2$ is phenylene, biphenylene or fluorenylene.

9. The aromatic amine compound as described in claim 1, wherein in Formula (2) described above, $R_1$ is phenyl, naphthyl or phenanthrene.

10. An organic electroluminescence device in which an organic thin film layer comprising a single layer or plural layers including at least a light emitting layer is interposed between a cathode and an anode, wherein at least one layer in the above organic thin film layer contains the aromatic amine derivative as described in claim 1 in the form of a single component or a mixed component.

11. The organic electroluminescence device as described in claim 1, wherein the above organic thin film layer comprises a hole transporting layer, and the aromatic amine derivative as described in claim 1 is contained in the above hole transporting layer.

12. The organic electroluminescence device as described in claim 1, wherein the above organic thin film layer comprises plural hole transporting layers, and the aromatic amine derivative as described in claim 1 is contained in the hole transporting layer which is not brought into direct contact with the light emitting layer.

13. The organic electroluminescence device as described in claim 1, wherein the above organic thin film layer comprises a hole injecting layer, and the aromatic amine derivative as described in claim 1 is contained in the above hole injecting layer.

14. The organic electroluminescence device as described in claim 1, wherein the aromatic amine derivative as described in claim 1 is contained in the hole injecting layer as a main component.

15. The organic electroluminescence device as described in claim 1, wherein a styrylamine compound and/or an arylamine compound are contained in the light emitting layer.

16. The organic electroluminescence device as described in claim 1, wherein a layer brought into contact with the anode which is present in the hole injecting layer described above is a layer containing an acceptor material.

17. The organic electroluminescence device as described in claim 1, wherein it emits light of a blue color.

18. The aromatic amine compound of claim 1, wherein at least one of $Ar_1$-$Ar_4$ is represented by formula (2) and the other $Ar_1$-$Ar_4$ are each, independently, selected from the group consisting of phenyl, biphenyl, fluorenyl and terphenyl; $L_1$ and $L_2$ are each, independently, selected from the group consisting of phenylene, biphenylene and fluorenylene; and $R_1$ is at least one selected from the group consisting of phenyl, naphthyl, and phenanthrene.

19. The aromatic amine compound of claim 18, wherein at least one of $Ar_1$-$Ar_4$ is a terphenyl group.

20. The aromatic amine compound of claim 1, wherein $L_1$ is biphenylene, at least one of $Ar_1$-$Ar_4$ is represented by formula (2) and the other $Ar_1$-$Ar_4$ are each independently selected from the group consisting of phenyl and biphenyl; $L_2$ is phenyl; and $R_1$ is phenyl.

* * * * *